(12) United States Patent
Keyer et al.

(10) Patent No.: US 8,663,298 B2
(45) Date of Patent: Mar. 4, 2014

(54) POLYAXIAL BONE FIXATION ELEMENT

(75) Inventors: Thomas Keyer, West Chester, PA (US); Joseph Capozzoli, Mount Laurel, NJ (US); Eric McDivitt, Schwenksville, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 316 days.

(21) Appl. No.: 12/669,224

(22) PCT Filed: Jul. 21, 2008

(86) PCT No.: PCT/US2008/070670
§ 371 (c)(1),
(2), (4) Date: Jan. 15, 2010

(87) PCT Pub. No.: WO2009/015100
PCT Pub. Date: Jan. 29, 2009

(65) Prior Publication Data
US 2010/0198272 A1 Aug. 5, 2010

Related U.S. Application Data

(60) Provisional application No. 60/950,995, filed on Jul. 20, 2007, provisional application No. 60/988,584, filed on Nov. 16, 2007.

(51) Int. Cl.
*A61B 17/86* (2006.01)
(52) U.S. Cl.
USPC .................. 606/305; 606/304; 606/306
(58) Field of Classification Search
USPC ................................ 606/304–308
See application file for complete search history.

(56) References Cited

U.S. PATENT DOCUMENTS

| 4,863,383 | A | 9/1989 | Grafelmann | 433/174 |
| 4,936,851 | A | 6/1990 | Fox | 623/16.11 |

(Continued)

FOREIGN PATENT DOCUMENTS

| EP | 1248573 A1 | 10/2002 |
| EP | 1316295 A2 | 6/2003 |

(Continued)

OTHER PUBLICATIONS

Aebi et al., "AO ASIF Principles in Spine Surgery", Springer, ©1998, 7 pages.
International Patent Application No. PCT/US2008/070670: International Search Report dated Feb. 17, 2009, 5 pages.
International Patent Application No. PCT/US2008/070670: International Preliminary Report on Patentability, 11 pages.

*Primary Examiner* — Eduardo C. Robert
*Assistant Examiner* — Julianna N Harvey
(74) *Attorney, Agent, or Firm* — Baker & Hostetler LLP

(57) ABSTRACT

The present invention is directed a polyaxial bone fixation element for use in spinal fixation to interconnect a longitudinal spinal rod with a patient's vertebra. The polyaxial bone fixation element preferably includes a bone anchor, a collet, a body, and a locking cap. The polyaxial bone fixation element preferably enables in-situ assembly. That is, the polyaxial bone fixation element is preferably configured so that in use, the bone anchor may be secured to the patient's vertebra prior to being received within the body. Accordingly, the polyaxial bone fixation element enables a surgeon to implant the bone anchor without the body to maximize visibility and access around the anchoring site. Once the bone anchor has been secured to the patient's vertebra, the body can be snapped-onto the bone anchor. The bone anchor preferably also includes a second tool interface so that a surgical instrument can be directly coupled to the bone anchor.

28 Claims, 13 Drawing Sheets

(56) References Cited

U.S. PATENT DOCUMENTS

| | | | | |
|---|---|---|---|---|
| 4,946,458 | A | 8/1990 | Harms | 606/305 |
| 5,116,337 | A * | 5/1992 | Johnson | 606/321 |
| 5,207,678 | A | 5/1993 | Harms | 606/267 |
| 5,474,555 | A | 12/1995 | Puno | 606/266 |
| 5,501,684 | A | 3/1996 | Schlapfer | 606/301 |
| 5,520,689 | A | 5/1996 | Schlapfer et al. | |
| 5,520,690 | A | 5/1996 | Errico et al. | |
| 5,527,183 | A | 6/1996 | O'Brien | 433/174 |
| 5,531,746 | A | 7/1996 | Errico et al. | |
| 5,534,001 | A | 7/1996 | Schlapfer | 606/302 |
| 5,549,608 | A | 8/1996 | Errico | 606/264 |
| 5,549,677 | A | 8/1996 | Durr | 623/16.11 |
| 5,554,157 | A | 9/1996 | Errico et al. | |
| 5,562,661 | A | 10/1996 | Yoshimi | 606/264 |
| 5,575,792 | A | 11/1996 | Errico | 606/276 |
| 5,578,033 | A | 11/1996 | Errico | 606/276 |
| 5,584,832 | A | 12/1996 | Schlapfer | |
| 5,584,834 | A | 12/1996 | Errico | 606/264 |
| 5,586,984 | A | 12/1996 | Errico | 606/264 |
| 5,601,429 | A | 2/1997 | Blacklock | 433/174 |
| 5,605,458 | A | 2/1997 | Bailey | 433/174 |
| 5,607,426 | A | 3/1997 | Ralph et al. | |
| 5,609,593 | A | 3/1997 | Errico | 606/276 |
| 5,609,594 | A | 3/1997 | Errico | 606/276 |
| 5,643,265 | A | 7/1997 | Errico et al. | |
| 5,647,873 | A | 7/1997 | Errico et al. | |
| 5,662,651 | A | 9/1997 | Tornier et al. | |
| 5,669,911 | A | 9/1997 | Errico | 606/264 |
| 5,683,392 | A | 11/1997 | Richelsoph | 606/272 |
| 5,688,273 | A | 11/1997 | Errico | 606/276 |
| 5,690,630 | A | 11/1997 | Errico | 606/264 |
| 5,704,939 | A | 1/1998 | Justin | 606/63 |
| 5,725,588 | A | 3/1998 | Errico et al. | |
| 5,728,098 | A | 3/1998 | Sherman | 606/269 |
| 5,733,285 | A | 3/1998 | Errico | 606/278 |
| 5,782,831 | A | 7/1998 | Sherman | 606/86 A |
| 5,797,911 | A | 8/1998 | Sherman | 606/270 |
| 5,817,094 | A | 10/1998 | Errico et al. | |
| 5,863,293 | A | 1/1999 | Richelsoph | 606/278 |
| 5,876,402 | A | 3/1999 | Errico et al. | |
| 5,879,350 | A | 3/1999 | Sherman | 606/270 |
| 5,882,350 | A | 3/1999 | Ralph et al. | |
| 5,885,286 | A | 3/1999 | Sherman | 606/270 |
| 5,888,204 | A | 3/1999 | Ralph et al. | |
| 5,899,940 | A | 5/1999 | Carchidi | 606/305 |
| 5,951,287 | A | 9/1999 | Hawkinson | 433/173 |
| 5,961,329 | A | 10/1999 | Stucki-McCormick | 433/173 |
| 5,964,760 | A | 10/1999 | Richelsoph | 606/279 |
| 6,010,503 | A | 1/2000 | Richelsoph | 606/278 |
| 6,017,177 | A | 1/2000 | Lanham | 411/410 |
| 6,053,917 | A | 4/2000 | Sherman | 606/270 |
| 6,074,391 | A | 6/2000 | Metz-Stavenhagen | 606/278 |
| 6,077,262 | A | 6/2000 | Schlapfer et al. | |
| 6,090,110 | A | 7/2000 | Metz-Stavenhagen | 606/270 |
| 6,126,662 | A | 10/2000 | Carmichael | 609/916 |
| 6,132,432 | A | 10/2000 | Richelsoph | 606/278 |
| 6,217,331 | B1 | 4/2001 | Rogers | 433/173 |
| 6,248,105 | B1 | 6/2001 | Schlapfer | 606/266 |
| 6,261,287 | B1 | 7/2001 | Metz-Stavenhagen | |
| 6,280,442 | B1 | 8/2001 | Barker | 606/60 |
| 6,355,040 | B1 | 3/2002 | Richelsoph | 606/272 |
| RE37,665 | E * | 4/2002 | Ralph et al. | 606/278 |
| 6,368,321 | B1 | 4/2002 | Jackson | 606/270 |
| 6,402,752 | B2 | 6/2002 | Schaffler-Wachter | 606/266 |
| 6,454,772 | B1 | 9/2002 | Jackson | |
| 6,485,491 | B1 | 11/2002 | Farris | 606/250 |
| 6,491,696 | B1 | 12/2002 | Kunkel | 606/105 |
| 6,537,070 | B1 | 3/2003 | Stucki-McCormick | 433/174 |
| 6,537,276 | B2 | 3/2003 | Metz-Stavenhagen | 606/272 |
| 6,558,387 | B2 | 5/2003 | Errico et al. | |
| 6,565,565 | B1 | 5/2003 | Yuan | 606/272 |
| 6,585,740 | B2 | 7/2003 | Schlapfer | 606/308 |
| 6,660,004 | B2 | 12/2003 | Barker | 606/328 |
| 6,716,214 | B1 | 4/2004 | Jackson | 606/266 |
| 6,770,075 | B2 | 8/2004 | Howland | 606/86 A |
| 6,780,186 | B2 | 8/2004 | Errico et al. | |
| 6,783,527 | B2 | 8/2004 | Drewry | 606/254 |
| 6,835,196 | B2 | 12/2004 | Biedermann et al. | |
| 6,843,791 | B2 | 1/2005 | Serhan | 606/272 |
| 6,869,433 | B2 | 3/2005 | Glascott | 606/308 |
| 6,887,275 | B2 | 5/2005 | Carchidi | 623/17.17 |
| 6,964,666 | B2 | 11/2005 | Jackson | 606/308 |
| 7,008,227 | B2 | 3/2006 | Carmichael | 433/174 |
| RE39,089 | E | 5/2006 | Ralph et al. | 606/278 |
| 7,128,743 | B2 | 10/2006 | Metz-Stavenhagen | 606/86 A |
| 7,163,539 | B2 | 1/2007 | Abdelgany | 606/86 A |
| 7,186,255 | B2 | 3/2007 | Baynham et al. | |
| 7,211,086 | B2 | 5/2007 | Biedermann et al. | |
| 7,250,052 | B2 | 7/2007 | Landry | 606/86 A |
| 7,316,684 | B1 | 1/2008 | Baccelli et al. | 606/61 |
| 7,967,849 | B2 | 6/2011 | Carson et al. | |
| 8,038,701 | B2 | 10/2011 | Rock et al. | |
| 8,197,517 | B1 | 6/2012 | Lab et al. | |
| 8,241,333 | B2 | 8/2012 | Jackson | |
| 2001/0047173 | A1 | 11/2001 | Schlapfer et al. | 606/72 |
| 2002/0045899 | A1 | 4/2002 | Errico et al. | |
| 2002/0103487 | A1 | 8/2002 | Errico et al. | |
| 2002/0120272 | A1 | 8/2002 | Yuan | 606/276 |
| 2003/0100896 | A1 | 5/2003 | Biedermann et al. | |
| 2003/0125742 | A1 | 7/2003 | Yuan | 606/279 |
| 2004/0024464 | A1 | 2/2004 | Errico et al. | |
| 2004/0143265 | A1 | 7/2004 | Landry | 606/86 A |
| 2004/0172022 | A1 | 9/2004 | Landry | 606/86 A |
| 2004/0193160 | A1 | 9/2004 | Richelsoph | 74/470 |
| 2004/0225292 | A1 | 11/2004 | Sasso et al. | |
| 2004/0236330 | A1 | 11/2004 | Purcell et al. | 606/266 |
| 2005/0049588 | A1 | 3/2005 | Jackson | 606/61 |
| 2005/0154391 | A1 | 7/2005 | Doherty | |
| 2005/0203516 | A1 | 9/2005 | Biedermann et al. | |
| 2005/0209592 | A1 | 9/2005 | Schlapfer et al. | 606/60 |
| 2005/0228385 | A1 | 10/2005 | Iott | 606/278 |
| 2005/0288671 | A1 | 12/2005 | Yuan | 606/279 |
| 2006/0004357 | A1 | 1/2006 | Lee | 606/278 |
| 2006/0084993 | A1 | 4/2006 | Landry | 606/86 A |
| 2006/0084996 | A1 | 4/2006 | Metz-Stavenhagen | 606/266 |
| 2006/0089643 | A1 | 4/2006 | Mujwid | 606/328 |
| 2006/0129149 | A1 | 6/2006 | Iott | 606/278 |
| 2006/0142761 | A1 | 6/2006 | Landry | 606/250 |
| 2006/0149233 | A1 | 7/2006 | Richelsoph | 74/470 |
| 2006/0149241 | A1 | 7/2006 | Richelsoph | 74/470 |
| 2006/0149265 | A1 | 7/2006 | James et al. | |
| 2006/0155277 | A1 | 7/2006 | Metz-Stavenhagen | |
| 2006/0173456 | A1 | 8/2006 | Hawkes et al. | |
| 2006/0247636 | A1 | 11/2006 | Yuan | 606/279 |
| 2006/0293659 | A1 * | 12/2006 | Alvarez | 606/61 |
| 2006/0293664 | A1 | 12/2006 | Schumacher | |
| 2007/0016200 | A1 | 1/2007 | Jackson | 606/61 |
| 2007/0088357 | A1 | 4/2007 | Johnson | |
| 2007/0090238 | A1 | 4/2007 | Justis | 248/181.1 |
| 2007/0123870 | A1 | 5/2007 | Jeon | 606/328 |
| 2007/0135817 | A1 | 6/2007 | Ensign | 606/96 |
| 2007/0167949 | A1 | 7/2007 | Altarac et al. | |
| 2007/0250064 | A1 | 10/2007 | Darois | 606/284 |
| 2007/0270880 | A1 | 11/2007 | Lindemann | 606/104 |
| 2007/0288004 | A1 | 12/2007 | Alvarez | |
| 2008/0249570 | A1 | 10/2008 | Carson et al. | |
| 2008/0294202 | A1 | 11/2008 | Peterson et al. | |
| 2009/0149887 | A1 | 6/2009 | Schlaepfer et al. | |
| 2009/0198280 | A1 | 8/2009 | Spratt et al. | |
| 2010/0145394 | A1 | 6/2010 | Harvey et al. | |
| 2010/0198272 | A1 | 8/2010 | Keyer et al. | |
| 2011/0213424 | A1 | 9/2011 | Biedermann et al. | |
| 2011/0230917 | A1 | 9/2011 | Carson et al. | |
| 2011/0270325 | A1 | 11/2011 | Keyer et al. | |

FOREIGN PATENT DOCUMENTS

| | | |
|---|---|---|
| EP | 1323391 A2 | 7/2003 |
| EP | 0 674 880 | 10/2004 |
| JP | 2006-525102 A | 11/2006 |
| WO | WO 97/02786 | 1/1997 |
| WO | WO 98/52482 A1 | 11/1998 |
| WO | WO 00/21455 | 4/2000 |
| WO | WO 02/076314 A1 | 10/2002 |

(56) References Cited

FOREIGN PATENT DOCUMENTS

| WO | WO 2005/016161 A1 * | 2/2005 |
| WO | WO 2006/116437 A2 | 11/2006 |
| WO | WO 2007/038350 A2 | 4/2007 |
| WO | WO 2007/047711 A2 | 4/2007 |
| WO | WO 2007/146032 A2 | 12/2007 |
| WO | WO 2008/089096 A2 | 7/2008 |
| WO | WO 2009/015100 A2 | 1/2009 |
| WO | WO 2010/028287 A3 | 3/2010 |

* cited by examiner

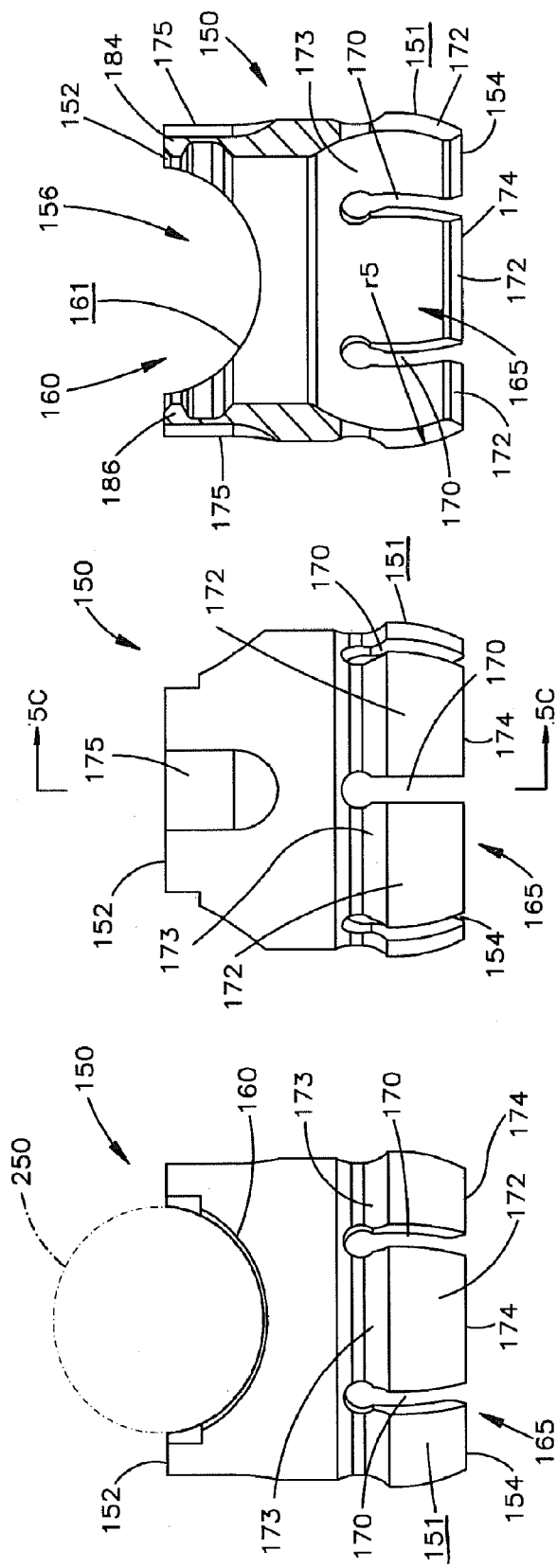

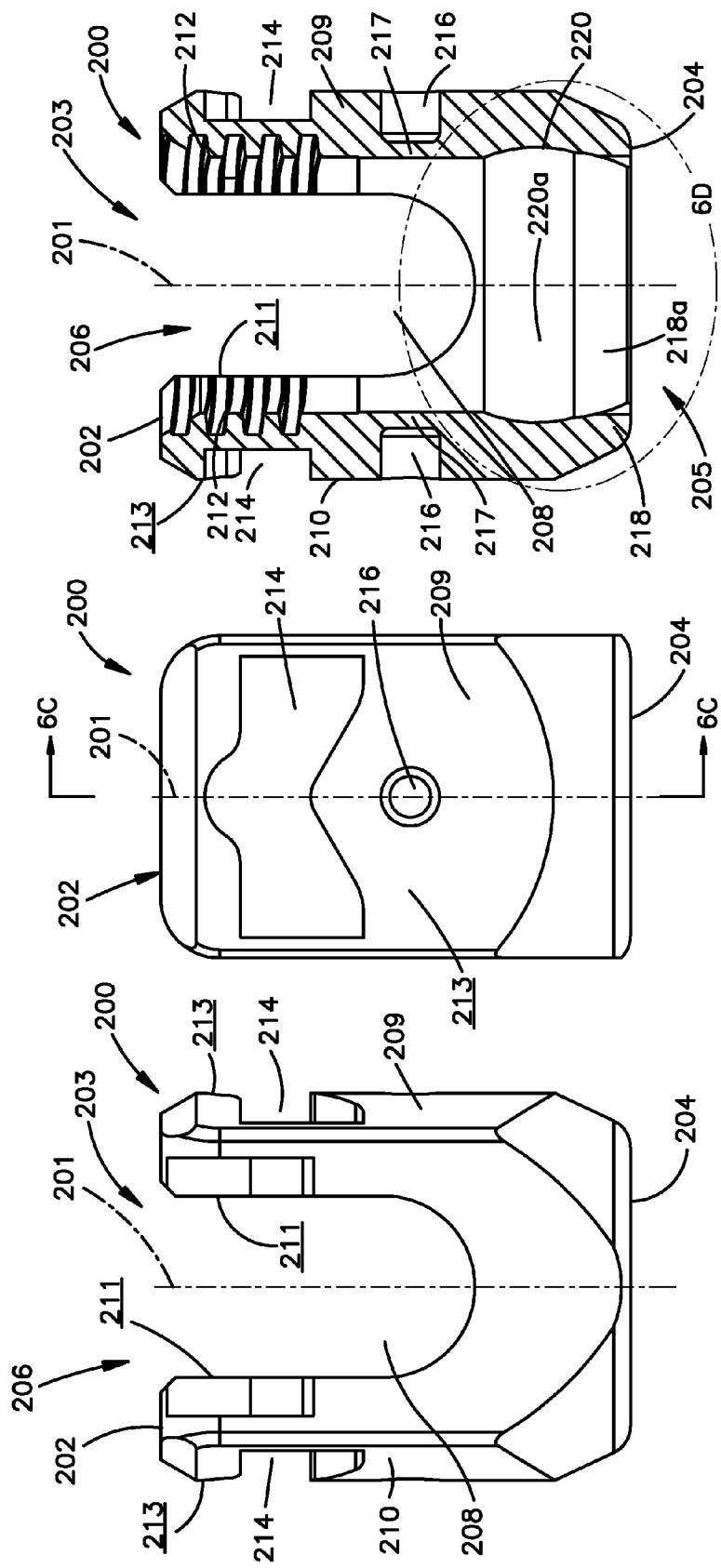

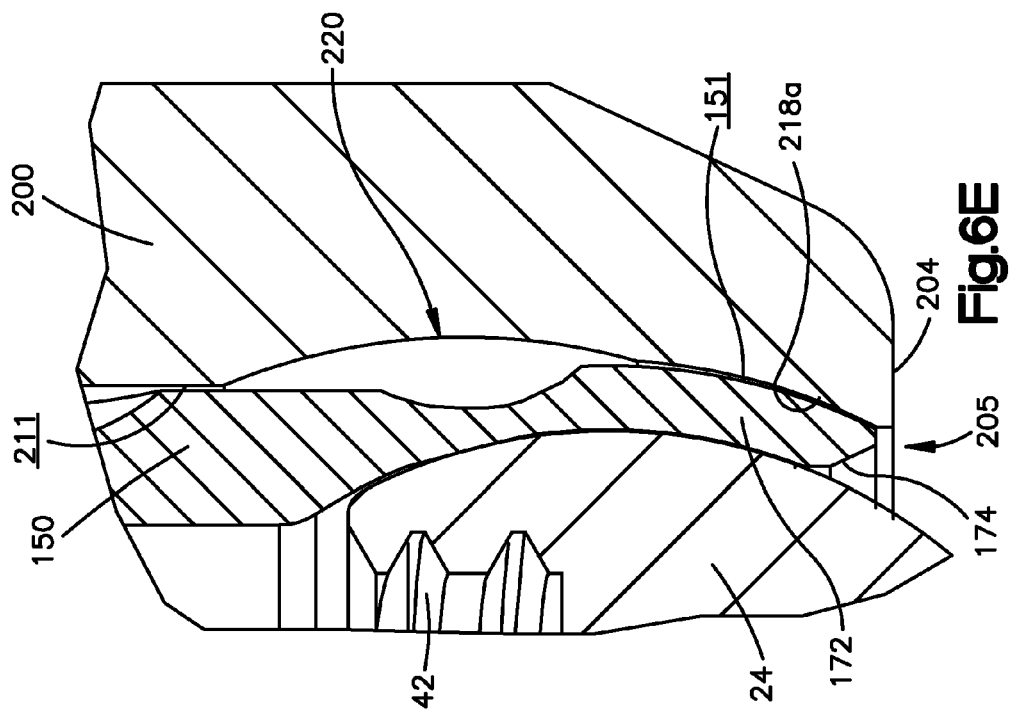
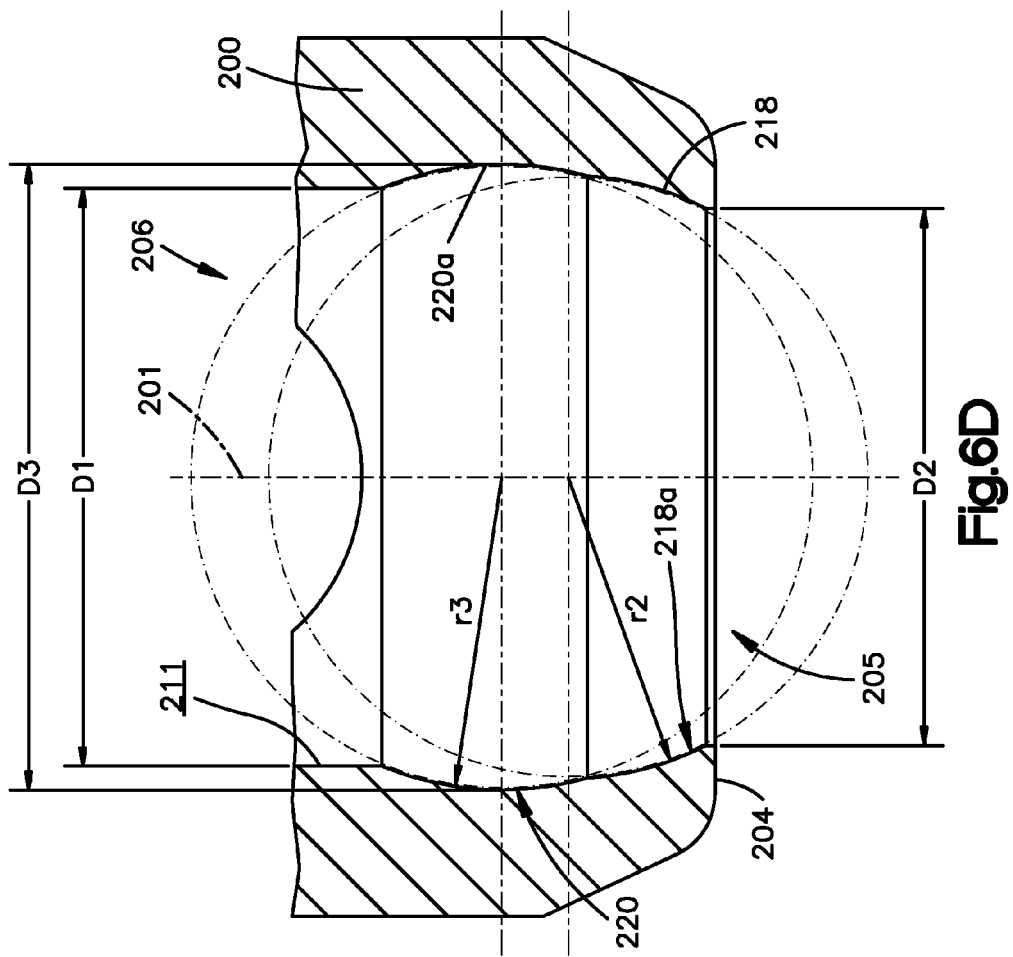

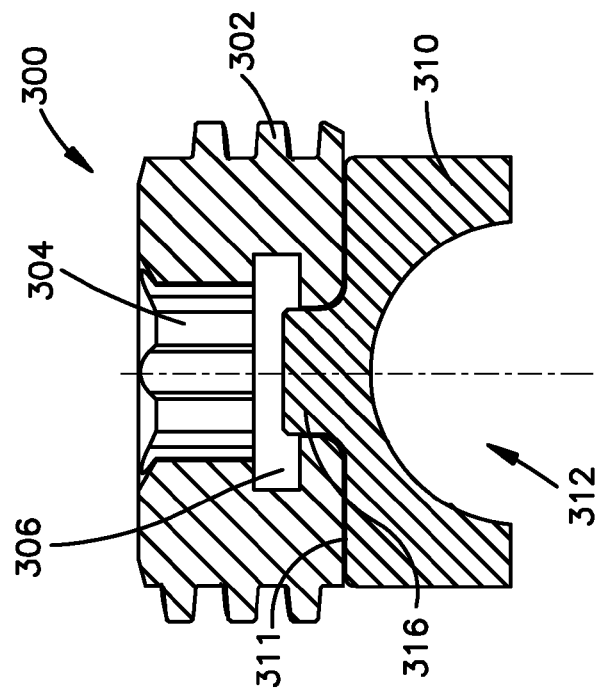
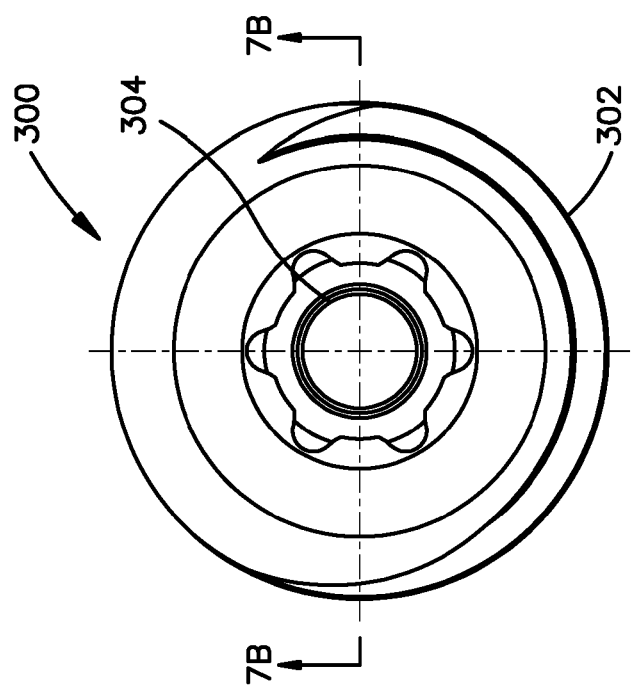

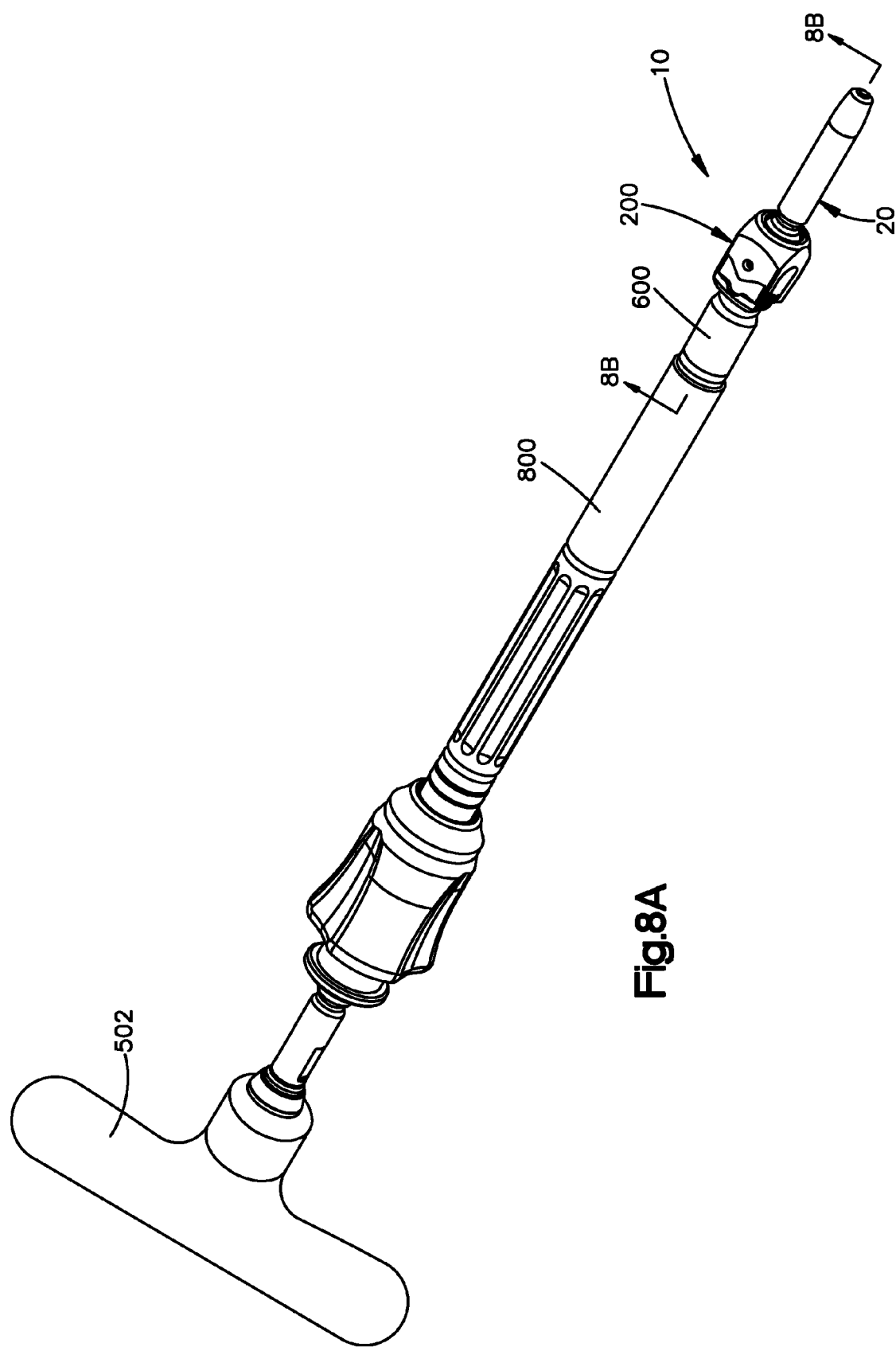

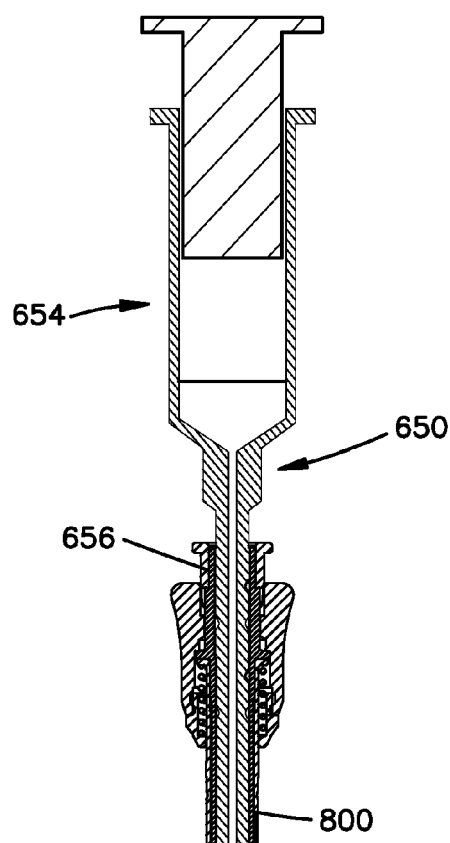
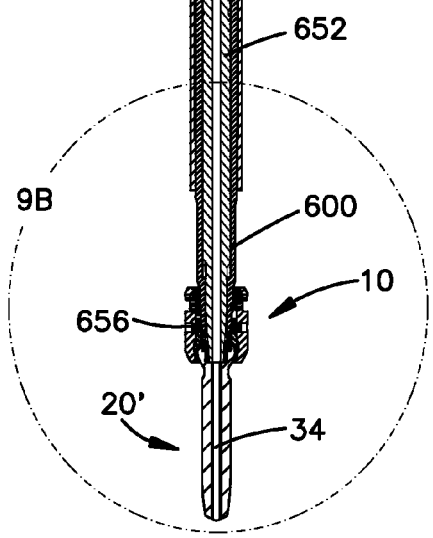
Fig.9A

POLYAXIAL BONE FIXATION ELEMENT

CROSS REFERENCE TO RELATED APPLICATIONS

This application is a national phase of PCT Application No. PCT/US2008/070670 filed Jul. 21, 2008, entitled "POLYAXIAL BONE FIXATION ELEMENT," which claims the benefit of U.S. Provisional Application No. 60/950,995, filed on Jul. 20, 2007, entitled "TOP-LOADING POLYAXIAL PEDICLE SCREW," and the benefit of U.S. Provisional Application No. 60/988,584, filed on Nov. 16, 2007, entitled "BONE SCREW WITH AN INSTRUMENT INTERFACE," the entire contents of which are incorporated herein by reference.

BACKGROUND OF THE INVENTION

It is often necessary due to various spinal disorders to surgically correct and stabilize spinal curvatures, or to facilitate spinal fusion. Numerous systems for treating spinal disorders have been disclosed.

One method involves a pair of elongated members, typically spinal rods, longitudinally placed on the posterior spine on either side of spinous processes of the vertebral column. Each rod is attached to various vertebrae along the length of the spine by way of pedicle screws. The pedicle screws each may include a body having a U-shaped rod-receiving channel for receiving a portion of the longitudinal spinal rod therein. Moreover, the body often interacts with a locking cap to clamp and secure the position of the spinal rod within the rod-receiving channel.

To facilitate insertion of the spinal rod into the rod-receiving channels and to provide additional flexibility in the positioning of the spinal rods and the pedicle screws, pedicle screws have been developed wherein the body is pivotable with respect to the bone anchor (commonly known as polyaxial pedicle screws).

It is desirable to develop a pedicle screw that is simple for a surgeon to use, provides for polyaxial rotation and is able to securely mount the rod to the selected vertebra.

SUMMARY OF THE INVENTION

A preferred embodiment of the present invention is directed to a polyaxial bone fixation element for use in a spinal fixation procedure. The polyaxial bone fixation element preferably includes a bone anchor having an enlarged head portion (e.g., a bone screw), a collet (e.g., an insert member), a body having an axial bore for receiving the collet and the enlarged head portion of the bone anchor. The body also includes a rod-receiving channel and threads for threadably receiving a locking cap (e.g., an externally threaded set screw). The polyaxial bone fixation element preferably enables in-situ assembly. That is, the polyaxial bone fixation element is preferably configured so that in use, the bone anchor may be secured to the patient's vertebra prior to being received within the body. Accordingly, the polyaxial bone fixation element preferably enables a surgeon to implant the bone anchor without the body and collet to maximize visibility and access around the anchoring site. Once the bone anchor has been secured to the patient's vertebra, the body can "pop-on" to the bone anchor. The bone anchor may also include an instrument interface so that a surgical instrument can be directly coupled to the bone anchor.

In one preferred embodiment, the polyaxial bone fixation element includes a bone anchor, a body, a collet and a locking cap. The bone anchor preferably includes an enlarged head portion. The head portion preferably includes a drive surface for engaging a first surgical instrument and an instrument interface for engaging a second surgical instrument. The body preferably includes a longitudinal axis, an upper end with an upper opening, a lower end with a lower opening, a bore extending between the upper opening and the lower opening wherein the bore has a first diameter, and a rod-receiving channel for receiving the spinal rod. The rod-receiving channel has a channel axis that is oriented substantially perpendicular to the longitudinal axis. The body preferably also includes a lower edge portion adjacent the lower opening. The lower edge portion has a second diameter smaller than the first diameter. The collet preferably includes a first end, a second end and one or more slots extending from the second end, wherein the slots define a plurality of flexible arms. The collet is preferably movably positioned within the bore of the body. The locking cap is preferably removably engageable with the body. The locking cap is movable from an unlocked position to a locked position, wherein movement of the locking cap from the unlocked position to the locked position urges the rod against the collet and the flexible arms against the lower edge portion to secure a position of the bone anchor relative to the body.

In another preferred embodiment, the polyaxial bone fixation element includes a body sized and configured to snap onto a head portion of an implanted bone anchor. The body preferably includes a longitudinal axis, an upper end with an upper opening, a lower end with a lower opening, a bore extending between the upper and lower openings wherein the bore has a first diameter, and a rod-receiving channel extending from the upper end toward the lower end and positioned on a channel axis that is oriented substantially perpendicular to the longitudinal axis. The bore preferably includes a lower edge portion terminating proximate the lower end and an enlarged diameter portion disposed adjacent to the lower edge portion and between the lower edge portion and the upper end. The lower edge portion preferably has a second diameter while the enlarged diameter portion has a third diameter, wherein the third diameter is preferably larger than the first diameter, which is larger than the second diameter. The collet preferably includes a first end, a second end and one or more slots extending from the second end, wherein the slots define a plurality of flexible arms. The flexible arms preferably each have a root end, a terminal end and a generally spherical, external surface proximate the terminal end. The flexible arms render the collet expandable to accept the head of the bone anchor and compressible to secure the head of the bone anchor relative to the collet. The flexible arms are preferably positioned proximate the enlarged diameter portion in a loading position and at least a portion of the external surface of the flexible arms contact the lower edge portion in a locked position.

In an alternate preferred embodiment, the polyaxial bone fixation element preferably includes a bone anchor, a body and a collet. The bone anchor preferably includes a head portion, wherein the head portion includes a drive surface for engaging a first surgical instrument and an instrument interface for engaging a second surgical instrument. The body preferably includes a longitudinal axis, an upper end with an upper opening, a lower end with a lower opening, a bore extending between the upper and lower openings, and a rod-receiving channel extending from the upper end toward the lower end and positioned on a channel axis that is oriented substantially perpendicular to the longitudinal axis. The bore preferably also includes a lower edge portion proximate the lower end and an enlarged diameter portion adjacent to the lower edge portion and between the lower edge portion and the upper end. The collet is preferably movably positioned within the bore of the body. The collet preferably includes a first end, a second end and one or more slots extending from the second end, wherein the slots define a plurality of flexible arms. The flexible arms preferably render the collet expandable to accept the head of the bone anchor and compressible to secure the head of the bone anchor relative to the collet. The collet preferably further includes a cavity extending from the second end. The flexible arms of the collet are preferably positioned in general vertical alignment with the enlarged diameter portion in a loading position so that the head of the bone anchor can be received in the cavity formed in the collet. At least a portion of the flexible arms preferably contact the lower edge portion in a locked position so that the head of the bone anchor is secured with respect to the collet. In the locked position, the contact is generally a line contact between the collet and the body.

BRIEF DESCRIPTION OF THE SEVERAL VIEWS OF THE DRAWINGS

The foregoing summary, as well as the following detailed description of a preferred embodiment of the application, will be better understood when read in conjunction with the appended drawings. The preferred embodiment of the polyaxial bone fixation element is shown in the drawings for the purposes of illustration. It should be understood, however, that the application is not limited to the precise arrangements and instrumentalities shown. In the drawings:

FIG. 5A illustrates a front elevational view of a collet used in connection with the polyaxial bone fixation element shown in FIG. 1;

FIG. 5B illustrates a side elevational view of the collet shown in FIG. 5A;

FIG. 5C illustrates a cross-sectional view of the collet shown in FIG. 5A, taken along line 5C-5C of FIG. 5B;

FIG. 6A illustrates a front elevational view of a first preferred embodiment of a body used in connection with the polyaxial bone fixation element shown in FIG. 1;

FIG. 6B illustrates a side elevational view of the body shown in FIG. 6A;

FIG. 6C illustrates a cross-sectional view of the body shown in FIG. 6A, taken along line 6C-6C of FIG. 6B;

FIG. 6D illustrates a magnified, cross-sectional view of a lower end of the body shown in FIG. 6A, taken from within circle 6D of FIG. 6C;

FIG. 6E illustrates a magnified, cross-sectional view of the lower end of the body shown in FIG. 6D and a collet and head of a bone anchor of the polyaxial bone fixation element shown in FIG. 1;

FIG. 7A illustrates a top plan view of a locking cap used in connection with the polyaxial bone fixation element shown in FIG. 1;

FIG. 7B illustrates a cross-sectional view of the locking cap shown in FIG. 7A, taken along line 7B-7B of FIG. 7A;

FIG. 8A illustrates a side perspective view of a preferred embodiment of a screw driver and a sleeve coupled to a portion of the polyaxial bone fixation element of FIG. 1;

FIG. 9A illustrates a cross-sectional view of a syringe assembly and the sleeve coupled to a portion of the polyaxial bone fixation element of FIG. 1.

DETAILED DESCRIPTION OF THE INVENTION

Figure 1:
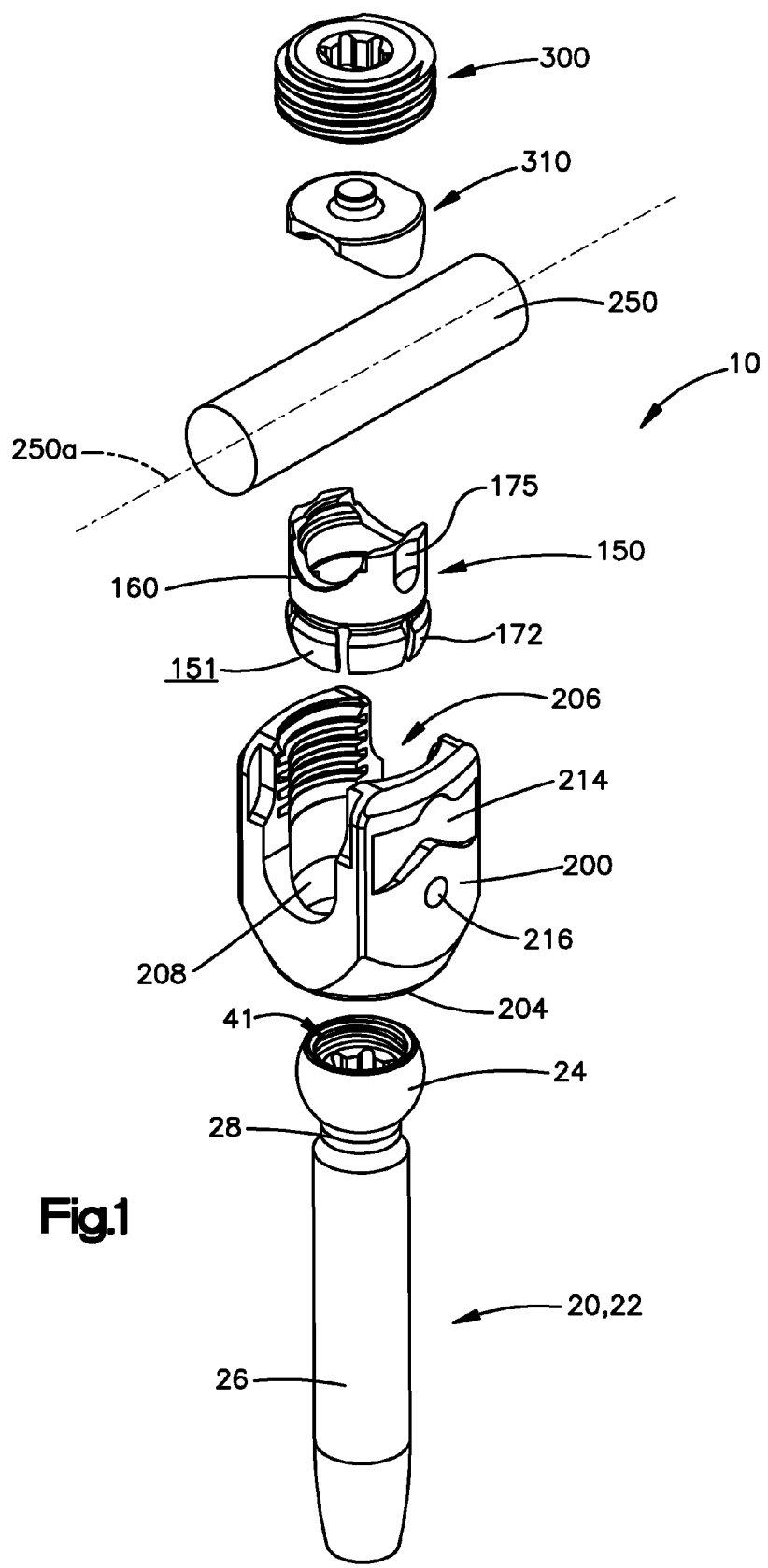
FIG. 1 illustrates an exploded, perspective view of a preferred embodiment of a polyaxial bone fixation element.
Figure 2:
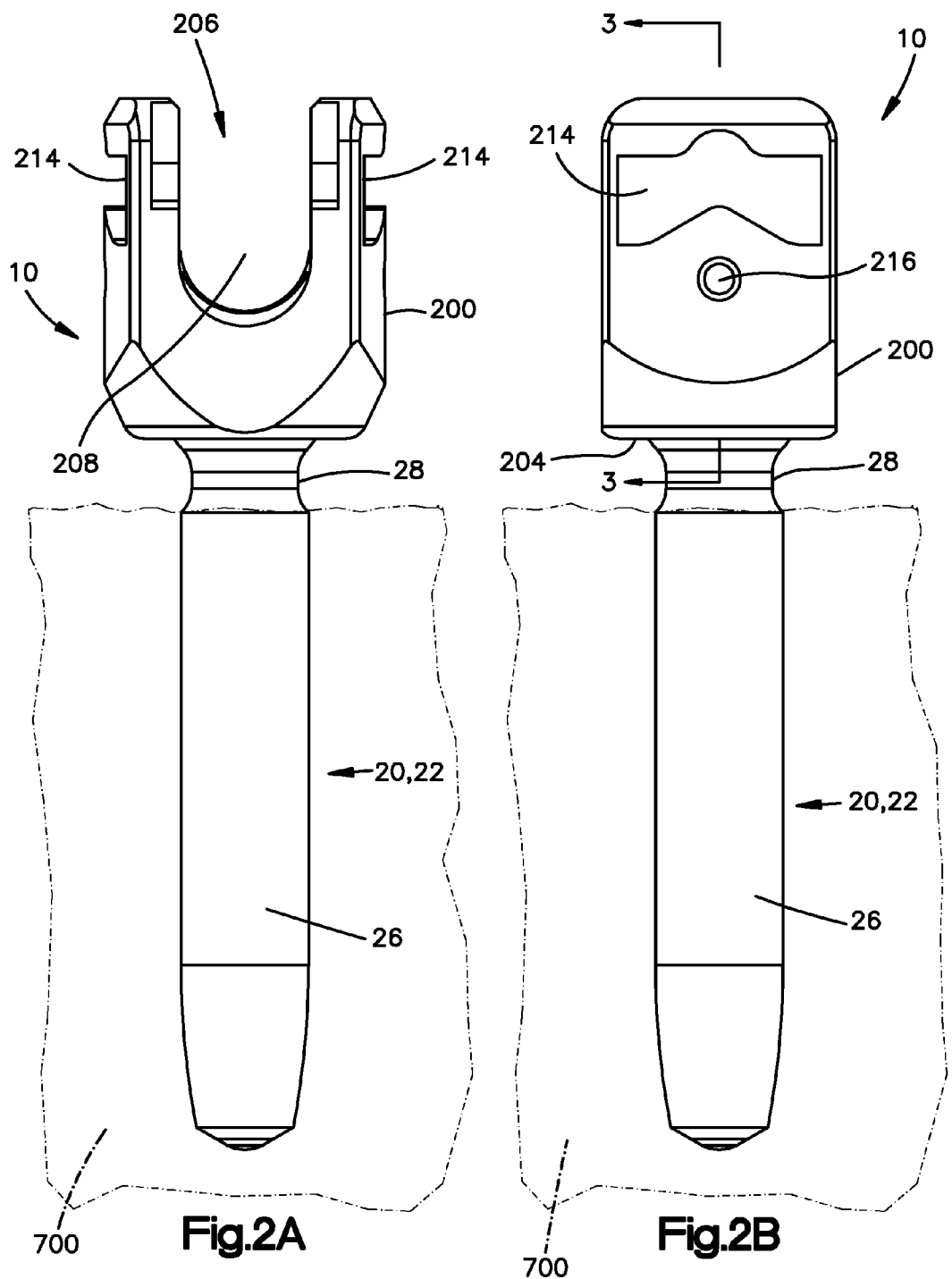
FIG. 2A illustrates a front elevational view of a portion the polyaxial bone fixation element shown in FIG. 1, mounted in a patient's vertebra.
FIG. 2B illustrates a side elevational view of the portion of the polyaxial bone fixation element shown in FIG. 1, mounted in the patient's vertebra.
Figure 3:
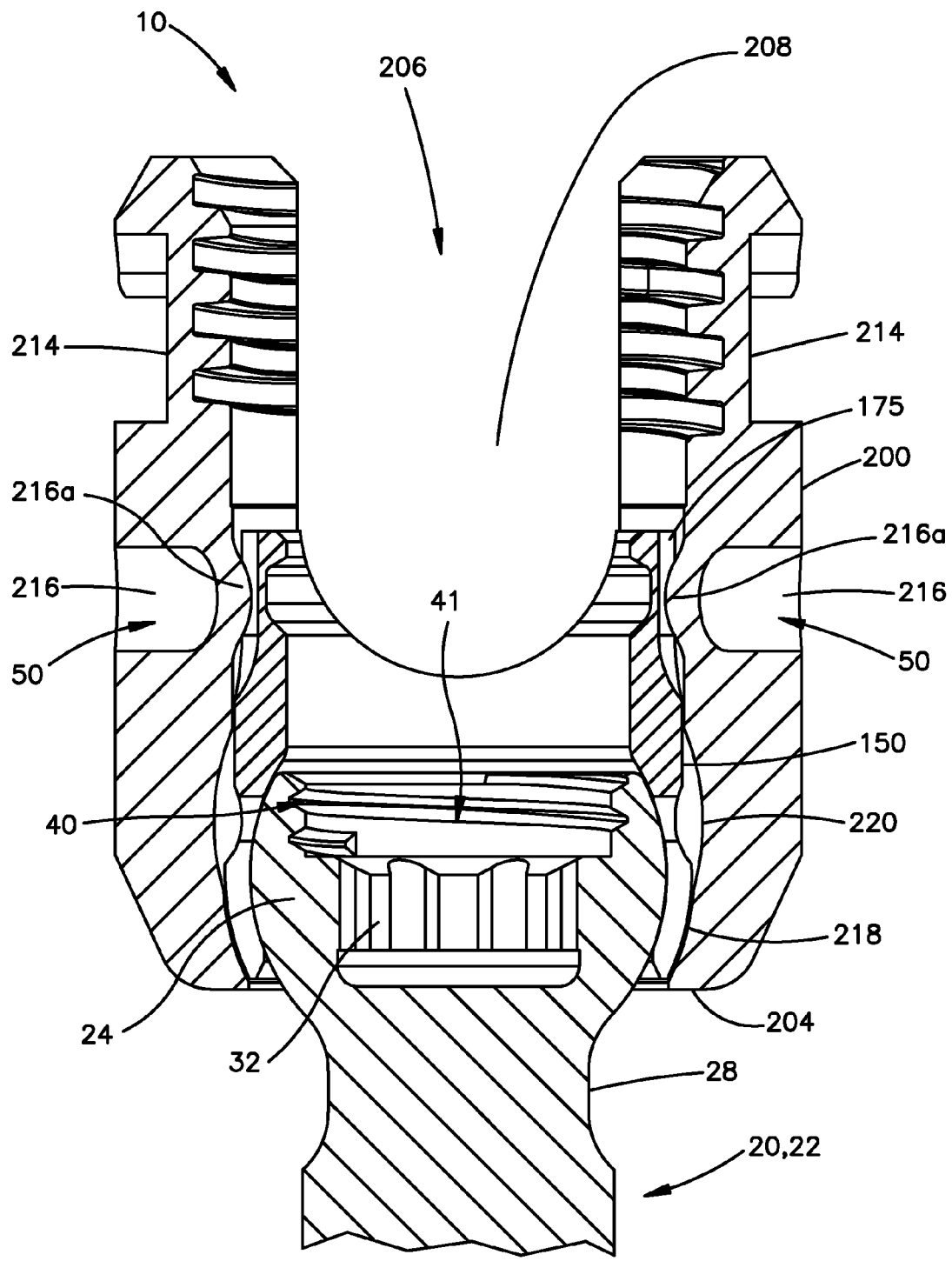
FIG. 3 illustrates a partial, cross-sectional view of the polyaxial bone fixation element shown in FIG. 1, taken along line 3-3 of FIG. 2B.
Figure 4A:
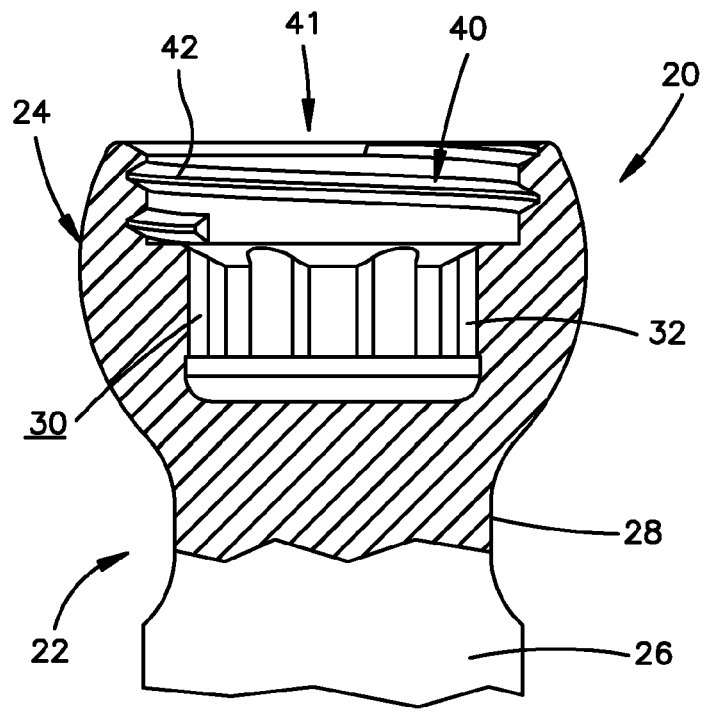
FIG. 4A illustrates a magnified cross-sectional view of a head portion of a bone anchor used in connection with the polyaxial bone fixation element shown in FIG. 1.
Figure 4B:
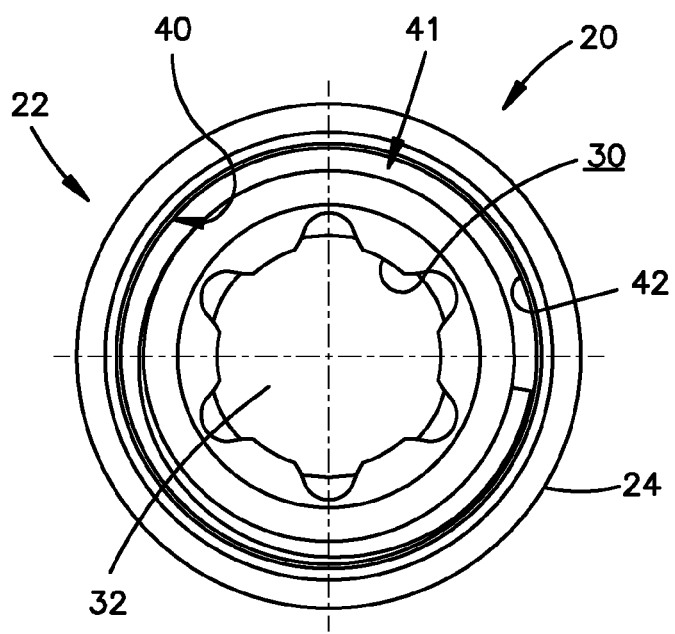
FIG. 4B illustrates a top plan view of the bone anchor shown in FIG. 4A.
Figure 6G:
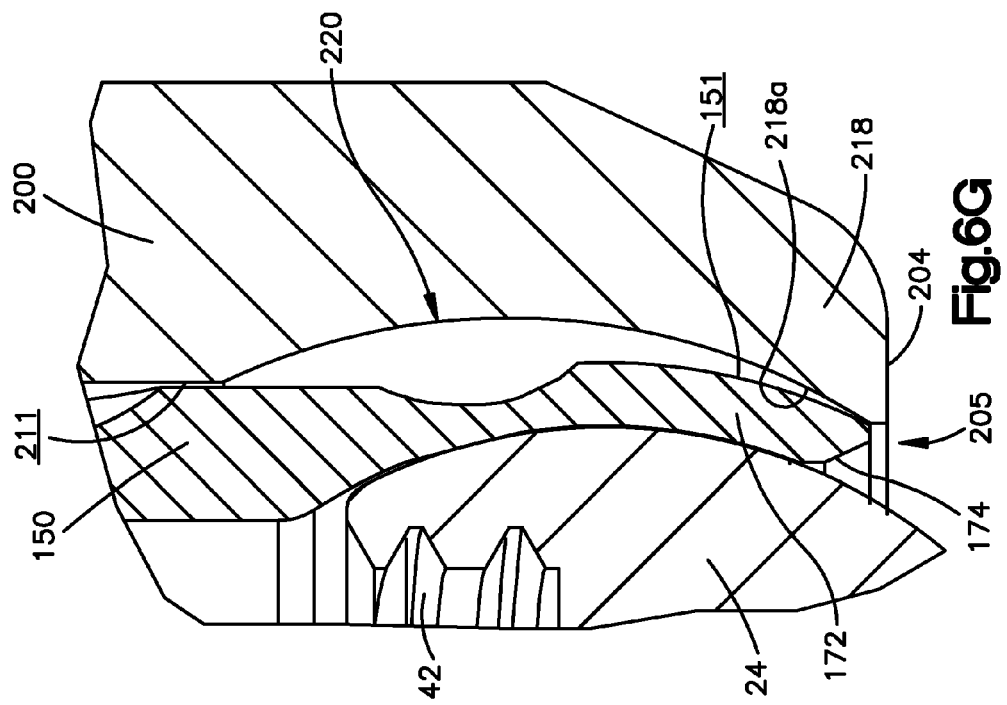
FIG. 6G illustrates a magnified, cross-sectional view of the lower end of the body shown in FIG. 6F.
Figure 6F:
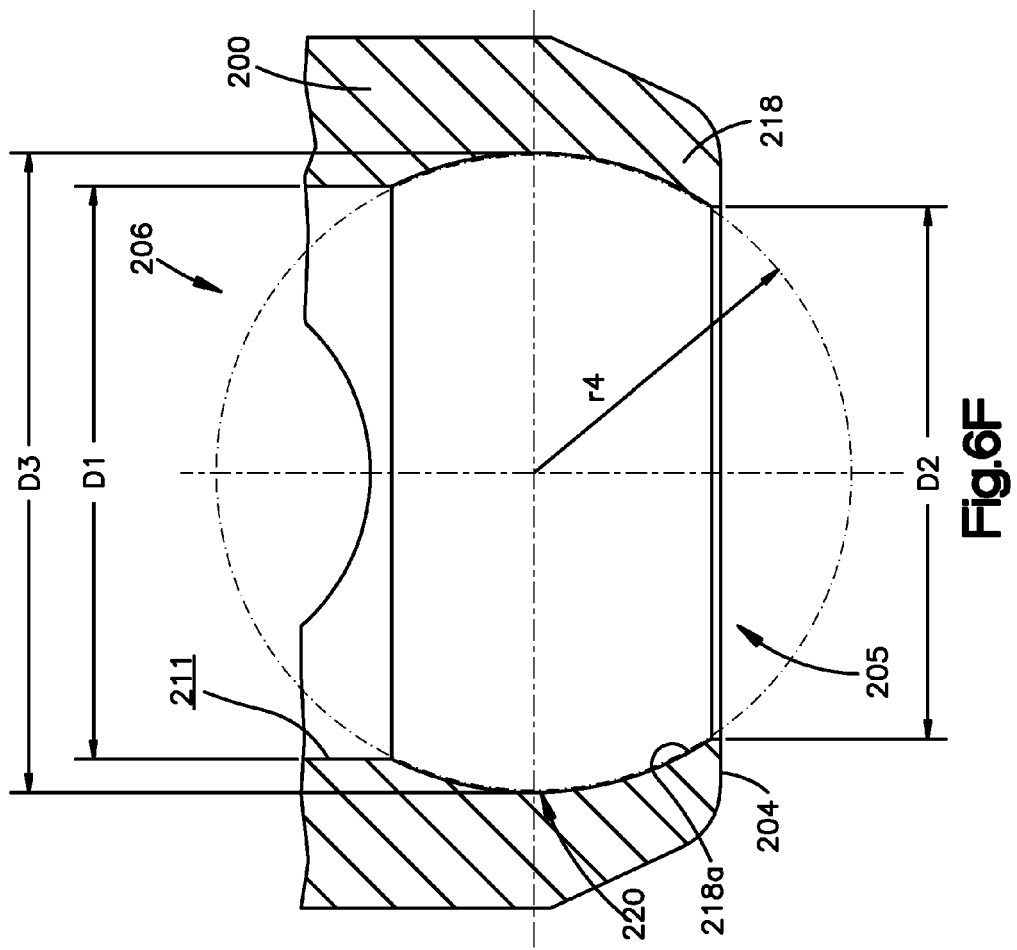
FIG. 6F illustrates a magnified, cross-sectional view of a second preferred embodiment of a lower end of a body of the polyaxial bone fixation element shown in FIG. 1.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the polyaxial bone fixation element, the described instruments and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. In general, such embodiments relate to a preferred polyaxial bone fixation element, and related instruments by way of non-limiting example and a polyaxial bone fixation element for use in spinal fixation to facilitate insertion of a longitudinal spinal rod in a rod-receiving channel formed in the body of the polyaxial bone fixation element. The invention may have other applications and uses and should not be limited to the structure or use described and illustrated.

Referring to FIGS. 1-7B, a preferred polyaxial bone fixation element 10 includes a bone anchor 20 (shown as a bone screw), a collet 150, a body 200, and a locking cap 300 (shown as an externally threaded set screw). As will be described in greater detail below, the polyaxial bone fixation element 10 preferably enables in-situ assembly. That is, preferably, the polyaxial bone fixation element 10 is configured so that in use, the bone anchor 20 may be secured to a patient's vertebra 700 prior to being received within the body 200. The polyaxial bone fixation element 10 preferably enables a surgeon to implant the bone anchor 20 without the body 200 and collet 150 pre-assembled to the bone anchor 20. By enabling the surgeon to implant the bone anchor 20 only, the polyaxial bone fixation element 10 maximizes visibility and access around the anchoring site. Once the bone anchor 20 has been secured to the patient's vertebra 700, the body 200 and collet 150 may "pop-on" to the bone anchor 20. Accordingly, the preferred polyaxial bone fixation element 10 is typically considered a bottom loading device, because the bone anchor 20 enters the body 200 through a lower or bottom end 204. Alternatively, the polyaxial bone fixation element 10 may be provided pre-assembled using identical components as described herein or may be configured for top loading with minor modifications, as would be apparent to one having ordinary skill in the art. Further, the collet 150 and body 200 assembly may be popped-off of the bone anchor 20 in-situ by arranging the collet 150 relative to the body 200 in a loading position, after the fixation element 10 has been arranged in the locked position, and removing the assembly from the bone anchor 20, as will be described in greater detail below.

While the polyaxial bone fixation element 10 will be described as and may generally be used in the spine (for example, in the lumbar, thoracic or cervical regions), those skilled in the art will appreciate that the polyaxial bone fixation element 10 may be used for fixation of other parts of the body such as, for example, joints, long bones or bones in the hand, face, feet, extremities, cranium, etc.

As will be described in greater detail below, several polyaxial bone fixation elements 10 may be used to secure a longitudinal spinal rod 250 to several vertebrae 700. It should be understood that the spinal rod 250 may include, but is not limited to, a solid rod, a non-solid rod, a flexible or dynamic rod, etc. It should be understood that the polyaxial bone fixation element 10 is not limited in use to any particular type of spinal rod 250.

Referring to FIGS. 1-4B, the bone anchor 20 preferably is in the form of a bone screw 22. Alternatively, however, the bone anchor 20 may be, for example, a hook or other fastener such as, a clamp, an implant, etc.

The bone screw 22 preferably includes an enlarged, curvate head portion 24 and an externally threaded shaft portion 26 for engaging the patient's vertebra 700. The specific features of the shaft 26 including, for example, thread pitch, shaft diameter, shaft shape, etc. are interchangeable, and it would be apparent to one having ordinary skill in the art that the bone screw 22 is not limited to any particular type of shaft 26. The bone screw 22 may or may not be cannulated (See FIGS. 9A and 9B). The bone screw 22 may also include a reduced diameter neck portion 28 between the head portion 24 and the shaft portion 26, which accommodates the polyaxial nature of the bone fixation element 10. The bone screw 22 may further be cannulated and fenestrated (not shown) such that openings extend outwardly from a central hollow channel in a cannulated screw to urge fluid out of the screw during injection or draw fluid into the central hollow channel from sides of the screw during extraction of material adjacent the screw.

Referring to FIGS. 3-4B and 8A-9B, the enlarged curvate head portion 24 preferably has a curvate or semi-spherical shape to facilitate rotation with respect to the collet 150, as will be described in greater detail below. The head portion 24 also preferably includes a drive surface 30 for receiving a corresponding tip 501 formed on a drive tool, such as a screw driver 500 (FIGS. 8A and 8B) for rotating the bone screw 22 into engagement with the patient's vertebra 700. The drive surface 30 may have any form now or hereafter known including, but not limited to, an external hexagon, a star drive pattern, a Phillips head pattern, a slot for a screw driver, a threading for a correspondingly threaded post, etc. Preferably, as shown, the drive surface 30 is comprised of a first tool interface or an internal recess 32, but is not so limited and may be comprised of an external drive feature that engages a female-type driver (not shown). The specific shape of the drive surface 30 or first tool interface 32 may be chosen to cooperate with the corresponding drive tool.

The head portion 24 may also include a second tool interface or a sleeve interface 40. The second tool interface 40 may be in any form now or hereafter known including, but not limited to, an internal or external thread, an external hexagon, a star drive pattern, a Phillips head pattern, a slot for a screw driver, a groove, a slot, etc. Preferably, however, the second tool interface 40 includes a plurality of threads 42 for threadably engaging a surgical instrument, such as a sleeve 600 (FIGS. 8A-9B), bone augmentation instrumentation, aspiration instrumentation, reduction tool for sagittal reduction or other reduction, coronal rotation tool, soft tissue refraction tool, kyphosis and lordosis correction tool, etc. The second tool interface 40 of the preferred embodiment permits application of forces to the bone anchor 20 along a longitudinal axis of the bone anchor 20, as well as along or at angles to the axis. In the preferred embodiment, the sleeve 600 is adaptable for use in combination with at least the screw driver 500 and an injection assembly 650. The surgical instrument may alternatively be any surgical instrument now or hereafter used in connection with a spinal fixation procedure including, but not limited to, a compressor, a distractor, minimally invasive instrumentation, etc. By incorporating the second tool interface 40 into the head portion 24 of the bone anchor 20, the sleeve 600 is able to directly engage the bone anchor 20 thus eliminating the need for the sleeve 600 to engage the body 200 of the polyaxial bone fixation element 10 and thereby, limiting toggling between the sleeve 600, screw driver 500 and/or bone anchor 20 in a working configuration, as will be described in greater detail below. In addition, the preferred second tool interface 40 permits application of forces to the bone anchor 20 through the sleeve 600 or another tool that mates with the second tool interface 40 to manipulate the bone anchor 20 and potentially the bone that the bone anchor 20 is mounted in.

Referring to FIGS. 3-4B, 8B and 9B, the second tool interface 40 and the first tool interface 32 are preferably formed in a head interface cavity 41 exposed from the top end of the head 24. Exposing both the second tool interface 40 and the first tool interface 32 at the top end of the head 24 permits simultaneous engagement of instruments with the second tool interface 40 and first tool interface 32 for manipulating the bone anchor 20. Both the second tool interface 40 and the first tool interface 32 may be engaged individually or simultaneously by an instrument prior to mounting the collet 150 and body 200 to the head 24 or after the collet 150 and body 200 are mounted to the head 24 (See FIGS. 8B and 9B).

Referring to FIGS. 3 and 5A-5C, the collet 150 preferably includes a first or upper end 152 sized and configured to contact at least a portion of the spinal rod 250 (schematically depicted in FIG. 5A) when the spinal rod 250 is received within a rod-receiving channel 208 formed in the body 200 and a second or lower end 154 sized and configured to contact at least a portion of the head portion 24 of the bone anchor 20. More preferably, the upper end 152 of the collet 150 includes a seat 160 sized and configured to receive at least a portion of the spinal rod 250 when the spinal rod 250 is received within the rod-receiving channel 208 of the body 200. The lower end 154 of the collet 150 preferably includes an interior cavity 165 for receiving and securing the head portion 24 of the bone anchor 20 so that, as will be generally appreciated by one of ordinary skill in the art, the bone anchor 20 can polyaxially rotate through a range of angles with respect to the collet 150 and hence with respect to the body 200. The cavity 165 formed in the collet 150 preferably has a curvate or semi-spherical shape for receiving the curvate or semi-spherical head portion 24 of the bone anchor 20 so that the bone anchor 20 can polyaxially rotate with respect to the collet 150 and hence with respect to the body 200. Furthermore, at least a portion of the outer surface of the collet 150 is comprised of a curvate or spherical, convex surface 151 having a radius of curvature $r_5$ for contacting the inner surface 211 of the body 200, preferably the lower edge portion 218, as will be described in greater detail below.

The collet 150 preferably also includes one or more slots 170 (shown as a plurality of slots) extending from the lower end 154 thereof so that at least a portion of the collet 150 is: (i) radially expandable so that the head portion 24 of the bone anchor 20 can be inserted through the lower end 154 and into the cavity 165 of the collet 150 and (ii) radially compressible to compress or crush-lock against the head portion 24 of the bone anchor 20, in accordance with the application of radial forces applied thereto. In the preferred embodiment, the slots 170 define a plurality of flexible arms 172. Preferably each flexible arm 172 includes a root end 173 and a terminal end 174. The outer surface of the flexible arms 172 preferably include the curvate or spherical convex surface 151 of the collet 150 for defining a line-contact with the inner surface 211 of the body 200, preferably the first undercut 218a, as will be described in greater detail below.

The collet 150 may also include one or more grooves 175 formed on the outer surface thereof for engaging a projection or dimple 216a formed in the inner surface 211 of the body 200. As will be described in greater detail below, the collet 150 is permitted to float within the axial bore 206 formed in the body 200 between a loading position and a locked position. That is, the collet 150 is preferably movably positioned within the body 200 in an assembled configuration. Interaction between the one or more grooves 175 and the projection or dimples 216a prevents the collet 150 from moving out of the upper end 202 of the body 200 when in the loading position.

Figure 8B:
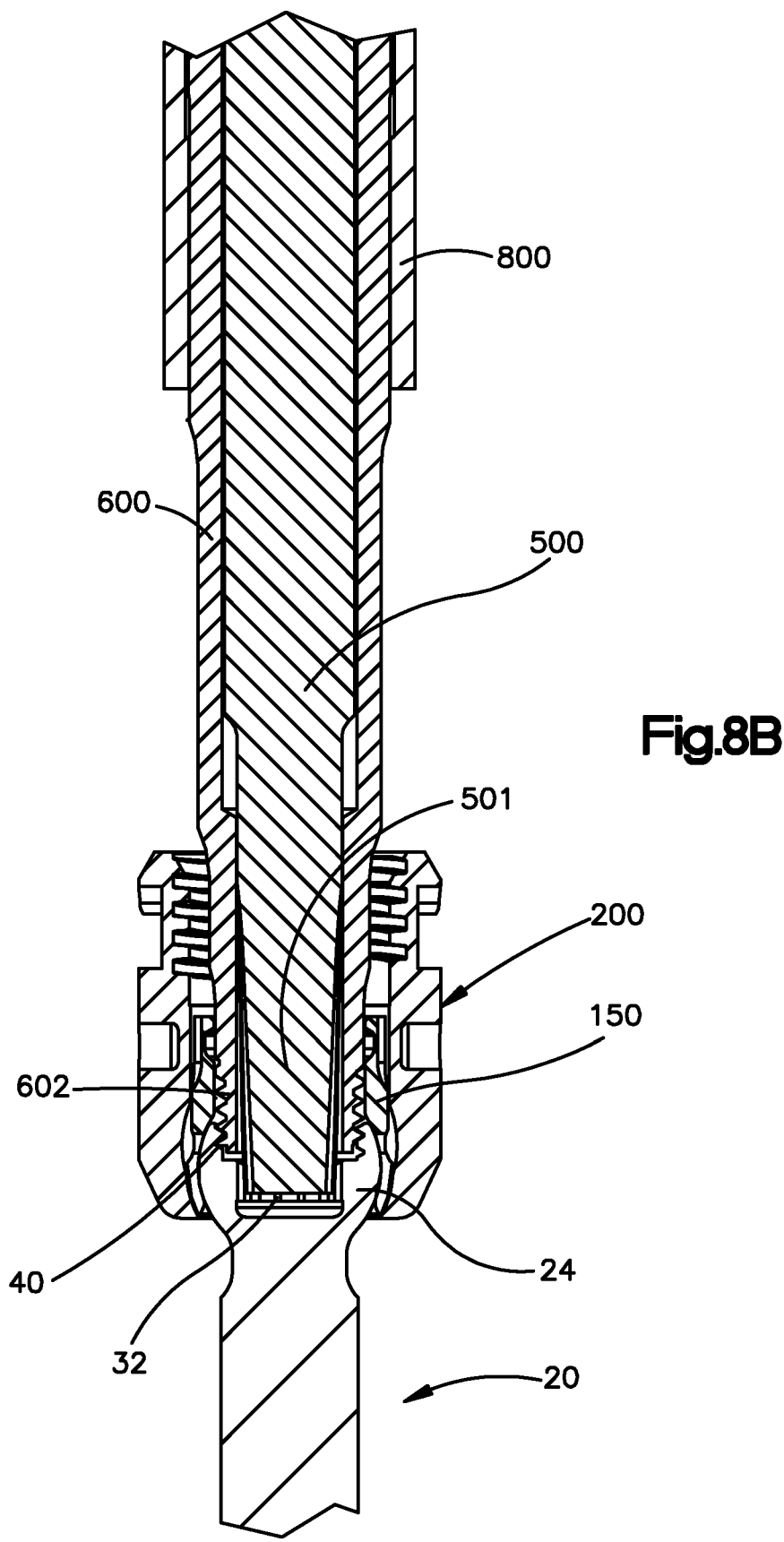
FIG. 8B illustrates a cross-sectional view of the screw driver and sleeve coupled to the portion of the polyaxial bone fixation element of FIG. 1, taken along line 8B-8B of FIG. 8A.
Figure 9B:
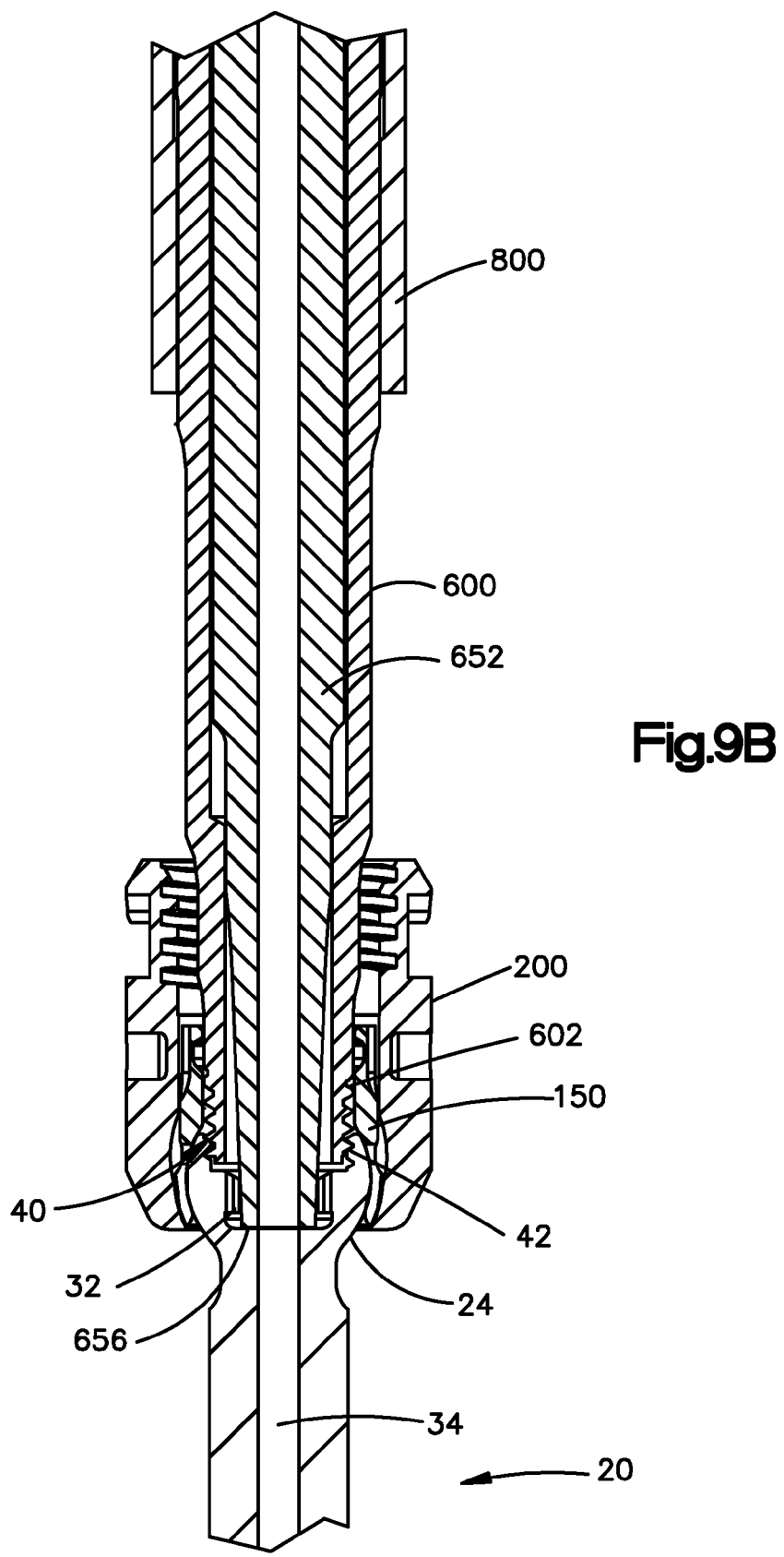
FIG. 9B illustrates a magnified, cross-sectional view of the syringe assembly and sleeve shown in FIG. 9A, taken from within the circle 9B of FIG. 9A.

The collet 150 also includes a bore 156 extending from the upper end 152 to the lower end 154 with an upper opening at the upper end 152 so that, for example, a drive tool, such as, for example, a screw driver 500, can be inserted through the collet 150 and into engagement with the bone anchor 20 so that the bone anchor 20 may be rotated into engagement with the patient's vertebra 700. The upper opening at the upper end 152 of the collet 150 also permits simultaneous insertion of the screw driver 500 and a second tool, such as the sleeve 600, therethrough to engage the head 24 (FIGS. 8B and 9B).

The collet 150 may also include one or more provisional rod-locking features so that the spinal rod 250 may be provisionally coupled to the collet 150, and hence with respect to the body 200. The provisional rod-locking features may be any mechanism now or hereafter developed for such purpose.

Referring to FIG. 5C, the collet 150 includes one or more inwardly projecting ledges 184, 186 disposed on an inner surface 161 of the seat 160 adjacent the upper end 152 of the collet 150. The ledges 184, 186 may be engaged by a tool (not shown) to apply a force between the collet 150 and the body 200 to move the collet 150 relative to the body 200. For example, the body 200 may be urged downwardly toward the bone anchor 20 relative to the collet 150 when the collet 150, body 200 and bone anchor 20 are in the locked position. Such application of a force may move the collet 150 from the locked position into the loading position, in situ, such that the flexible arms 172 are able to flex outwardly within an enlarged diameter portion 220 to permit the head 24 to move out of the cavity 165. Accordingly, the ledges 184, 186 may be utilized to disassemble the collet 150 and body 200 from the bone anchor 20 after the collet 150 and body 200 have been locked to the head 24.

Referring to FIGS. 6A-6D and 7A-7B, the body 200 may generally be described as a cylindrical tubular body having a longitudinal axis 201, an upper end 202 having an upper opening 203, a lower end 204 having a lower opening 205, and an axial bore 206 substantially coaxial with the longitudinal axis 201 of the body 200. The axial bore 206 extends from the upper opening 203 to the lower opening 205. The axial bore 206 preferably has a first diameter portion $D_1$ proximate the upper end 202. The body 200 also includes a substantially transverse rod-receiving channel 208 (shown as a top loading U-shaped rod-receiving channel) defining a pair of spaced apart arms 209, 210. The inner surface 211 of the spaced apart arms 209, 210 preferably includes a plurality of threads 212 for engaging a locking cap 300. Alternatively, the body 200 and, in particular, the spaced apart arms 209, 210 may have nearly any mounting receiving structure for engaging the locking cap 300 including, but not limited to, external threads, cam-lock, quarter lock, clamps, etc. The outer surface 213 of the spaced apart arms 209, 210 may each include a recess 214 for engaging one or more surgical instruments such as, for example, rocker forceps, a compressor, a distractor, a sleeve, minimally invasive instrumentation, etc.

Referring to FIGS. 5A-6E, the axial bore 206 preferably has the first diameter portion $D_1$ proximate the upper end 202. The inner surface 211 of the axial bore 206 preferably also includes a lower end portion 218 proximate the lower end 204 thereof. The lower end portion 218 defines a second diameter portion $D_2$, which is comprised of the smallest diameter portion of the axial bore 206. The second diameter portion $D_2$ is preferably defined by a first spherical undercut 218a adjacent the lower end 204 of the body 200. The first spherical undercut 218a preferably has a second radius of curvature $r2$ that is centered on the longitudinal axis 201 of the body 200. The second diameter portion $D_2$ is preferably smaller than the first diameter portion $D_1$ of the axial bore 206 such that the collet 150 may be inserted through the upper end 202 into the axial bore 206, but generally preventing the collet 150 from being inserted into the lower end 204 or from falling out of the lower end 204 once inserted into the axial bore 206.

The first spherical undercut 218a is preferably defined as a curvate or spherical concave surface for accommodating the outer curvate or spherical convex surface 151 of the collar 150. The first spherical undercut 218a and the spherical convex surface 151 preferably have a different radius of curvature such that line contact is defined between the surfaces 151, 218 when the collet 150 is positioned proximate the lower end 204. The second diameter portion $D_2$ is preferably sized and configured so that the enlarged head portion 24 of the bone anchor 20 may be passed through the lower opening 205 of the body 200, but is prevented from passing therethrough once the head portion 24 of the bone anchor 20 is received within the interior cavity 165 of the collar 150.

The inner surface 211 of the axial bore 206 preferably includes an enlarged portion 220 that is located toward the lower end 204 relative to the first diameter portion $D_1$. The enlarged portion 220 preferably defines a third diameter $D_3$ comprised of a curvate, preferably spherical, radially outwardly recessed portion. In the enlarged portion 220 of the axial bore 206, the third diameter $D_3$ is larger than the first diameter $D_1$ of the axial bore 206. In addition, the third diameter $D_3$ is larger than the second diameter $D_2$. In the preferred embodiment, the third diameter $D_3$ is defined by a second spherical undercut 220a.

The enlarged portion 220 is preferably located in between the upper end 202 and the lower end portion 218 and accommodates expansion of the flexible arm 172 therein when the head 24 is loaded into the collet 150, as will be described in greater detail below. The enlarged portion 220 is preferably in the form of a curvate or spherical concave surface having a third radius of curvature r3, which defines the third diameter $D_3$ at the largest diameter within the axial bore 206. The third radius of curvature r3 defines the spherical nature of the second spherical undercut 220a. The enlarged portion 220 is sized and configured so that when the collet 150 is placed in general alignment with the curvate or spherical concave surface of the enlarged portion 220, the flexible arms 172 of the collet 160 are permitted to radially expand within the axial bore 206 of the body 200 so that the head portion 24 of the bone anchor 20 can be inserted through the lower opening 205 formed in the body 200 and into the cavity 165 formed in the collet 150. More preferably, the enlarged portion 220 is sized and configured so that the outer curvate or spherical convex surface 151 of the collet 150 does not touch or contact the enlarged portion 220 of the body 200 when the head 24 is loaded into the collet 150. That is, the enlarged portion 220 formed in the body 200 is preferably sized and configured so that a gap remains between the outer curvate or spherical convex surface 151 of the collet 150 and the enlarged portion 220 of the body 200 even when the flexible arms 172 radially expand to accept the head portion 24 of the bone anchor 20. The enlarged portion 220 is not limited to constructions comprised of the preferred curvate or spherical undercut defined by the third radius of curvature r3 and may be constructed of nearly any undercut having nearly any shape that permits expansion of the collet 150 therein in the loading position to accept the head 24. For example, the enlarged portion 220 may be defined by a rectangular slot or groove on the inner surface 211 that results in the third diameter $D_3$ being larger than the first and second diameters $D_1$, $D_2$.

In the preferred embodiment, the second radius of curvature r2 of the first spherical undercut 218a is preferably different than an outer radius of curvature r5 of the outer curvate or spherical convex surface 151 of the collet 150 so a line contact results between the first spherical undercut 218a and the outer convex surface 151 when the collet 150 is positioned adjacent the lower end portion 218. That is, by providing non-matching radius of curvatures between the first spherical undercut 218a and the collet 150, only line contact occurs between the first spherical undercut 218a of the body 200 and the outer curvate or spherical convex surface 151 of the collet 150. The line contact between the body 200 and the collet 150 effectively pinches the lower ends of the flexible arms 172 onto the lower end of the head 24 below the greatest diameter of the head 24 to direct the lower end 154 beneath the largest diameter of the head 24, effectively locking the bone anchor 20 to the collet 150 in the locked position. In addition, the line contact between the collet 150 and body 200 permits disengagement of the collet 150 from the body 200 after the collet 150 and body 200 are engaged in the locked position or popping-off of the body 200 and collet 150 from the bone anchor 20, in situ.

Referring to FIGS. 5A-5C, 6F and 6G, the second and third diameters D2, D3 may be formed by a single internal radius of curvature r4 that undercuts the body 200 in the axial bore 206. The single internal radius of curvature r4 preferably permits expansion of the collet 150 to accept the head 24, insertion of the collet 150 into the axial bore 206 from the upper end 202 but not the lower end 204 and line contact between the outer curvate or spherical convex surface 151 of the collet and the lower end portion 218 when the collet 150 is in facing engagement with the lower end portion 218. In this configuration, the second diameter portion D2 is smaller than the first diameter portion D1, which is smaller than the third diameter portion D3.

Referring to FIGS. 1-3 and 5A-6C, the body 200 and collet 150 also preferably include a collet retention feature 50 so that once the collet 150 has been inserted into the bore 206 formed in the body 200 and, if necessary, the collet retention feature 50 has been engaged, the collet retention feature 50 inhibits the collet 150 from passing back through the upper opening 203 formed in the body 200, but permits some degree of vertical translation or floating of the collet 150 with respect to the body 200. That is, once inserted into the axial bore 206 of the body 200, the collet 150 is sized and configured to float or move within the axial bore 206 between a loading position and a locking position. The collet retention feature 50 preferably prevents the collet 150 from moving out of the upper opening 203 of the body 200. Preferably the collet retention feature 50 permits the flexible arms 172 to align with the enlarged portion 220 in the loading position when the lower edge of the grooves 175 come into contact with the dimples 216a. In addition, the collet 150 is preferably permitted to float between the loading position and the locking position prior to locking of the head 24 in the collet 150. Specifically, the collet 150 may float between the loading position where the dimples 216a are in contact with the lower edge of the grooves 175 and the locking position wherein the outer curvate or spherical convex surface 151 is in line contact with the lower end portion 218. The collet retention feature 50 preferably limits rotation of the collet 150 with respect to the body 200, because the dimples 216a slide within the grooves 175, so that the seat 160 formed in the collet 150 is aligned with the rod-receiving channel 208 formed in the body 200. However, the retention feature 50 is not limited to limiting rotation of the collet 150 with respect to the body 200 and may be configured to permit unlimited rotation of the collet 150 relative to the body 200 by eliminating the grooves 175 from the collet 150 and forming a shelf (not shown) around the collet 150 at the bottom end of the grooves 175 such that the dimples 216a engage the shelf to limit removal of the collet 150 out of the upper end 202 of the body 200, but permit unlimited rotation of the collet 150 relative to the body 200 in the assembled configuration.

The collet retention feature 50 may be any feature now or hereafter known for such purpose including, but not limited to, for example, an inwardly protruding shoulder or detent formed on the collet 150 for engaging corresponding indentations formed on the inner surface 211 of the body 200. In the preferred embodiment, the body 200 includes one or more partial passageways 216 formed therein so that once the collet 150 has been received within the axial bore 206 of the body 200, a force may be applied to the partial passageways 216 formed in the body 200 deforming the remaining portion of the partial passageway 217 into the dimple or projection 216a formed in the inner surface 211 of the body 200. That is, once the collet 150 has been received within the bore 206 of the body 200, an external force may be applied to the partial passageways 216 formed in the body 200 transforming the passageways 216 into the projections or dimples 216a that extend inwardly from the inner surface 211 of the spaced apart arms 209, 210 and into the bore 206 formed in the body 200. The dimples or projections 216a are preferably sized and configured to interact with the longitudinal groove 175 formed in the outer surface of the collet 150 so that the collet 150 is permitted to move with respect to the body 200 at least along the longitudinal axis 201, but inhibited from moving back through the upper opening 203 formed in the body 200. The collet 150 is also preferably partially inhibited from rotational movement with respect to the body 200. Movement of the collet 150 with respect to the body 200 toward the upper end 202 is preferably inhibited by the projections or dimples 216a contacting the bottom and/or lateral surfaces of the grooves 175. Limiting rotational movement of the collet 150 with respect to the body 200 permits alignment of the rod-receiving channel 208 and the seat 160 for receiving the rod 250, as will be described in greater detail below.

In use, positioning the collet 150 in general alignment with the curvate or spherical concave surface of the enlarged portion 220 in the loading position preferably enables the flexible arms 172 of the collet 150 to radially expand within the axial bore 206 of the body 200 so that the head portion 24 of the bone anchor 20 can be inserted through the lower opening 205 formed in the body 200 and into the cavity 165 formed in the collet 150. The enlarged portion 220 formed in the body 200 is preferably sized and configured so that a gap remains between the outer curvate or spherical convex surface 151 of the collet 150 and the enlarged portion 220 of the body 200 even when the flexible arms 172 radially expand to accept the head portion 24 of the bone anchor 20. Thereafter, movement of the collet 150 into general alignment and engagement with the first spherical undercut 218a of the lower end portion 218 causes a radial inward force to be applied to the flexible arms 172, which in turn causes the flexible arms 172 to compress against the head portion 24 of the bone anchor 20, thereby securing the position of the bone anchor 20 with respect to the collet 150 and hence with respect to the body 200. The lower end portion 218 and the outer curvate or spherical convex surface 151 of the collet 150 have non-matching radii of curvature r2, r4, r5 so that only line contact occurs between these components.

The head portion 24 of the bone anchor 20 and interaction of the dimples 216 with the grooves 175 preferably moves the collet 150 into alignment with the enlarged portion 220 as the head portion 24 is inserted through the lower opening 205 and into the axial bore 206. Moreover, the collet 150 is preferably moved into alignment and engagement with the lower edge portion 218 via engagement of the locking cap 300, as will be described in greater detail below.

Referring to FIGS. 7A and 7B, the locking cap 300 is preferably an externally threaded set screw 302 for threadably engaging the threads 212 formed on the inner surface 211 of the body 200. The externally threaded set screw 302 generally provides flexibility when inserting a spinal rod 250 into the body 200 such that the spinal rod 250 does not have to be completely reduced or seated within the body 200 prior to engagement of the cap 300. Incorporation of a threaded set screw 302 also enables the set screw 302 to reduce the spinal rod 250 during tightening of the locking cap with respect to the body 200. The locking cap 300 may be any locking cap now or hereafter developed for such purpose including, but not limited to, an externally threaded cap, a quarter-turn or partial-turn locking cap, two-piece set screw, etc.

As shown, the externally threaded set screw 302 preferably includes a drive surface 304 for engaging a corresponding drive tool for securing (e.g., threading) the set screw 302 onto the body 200. The drive surface 304 may take on any form now or hereafter developed for such purpose, including, but not limited to, an external hexagon, a star drive pattern, a Phillips head pattern, a slot for a screw driver, a threading for a correspondingly threaded post, etc. The drive surface 304 is preferably comprised of an internal recess. The specific shape of the internal recess may be chosen to cooperate with the corresponding drive tool. The drive surface 304 may also be configured to include the first and second tool interfaces 40, as were described above.

The externally threaded set screw 302 preferably also includes a saddle 310 operatively coupled thereto. The saddle 310 includes a transverse recess 312 formed therein for contacting at least a portion of the spinal rod 250. The rod-contacting surface of the recess 312 may include a surface finish (not shown) that adds roughness, such as, for example, a knurl, bead blasting, grooves, or other textured finish that increases surface roughness and enhances rod push through strength.

The saddle 310 may be coupled to the set screw 302 by any means now or hereafter developed for such purpose including, but not limited to, adhesion, mechanically fastening, etc. The set screw 302 preferably includes a bore 306 for receiving a stem 316 formed on a top surface 311 of the saddle 310. In use, the saddle 310 is preferably coupled to the set screw 302 but is free to rotate with respect to the set screw 302 so that the saddle 310 can self-align with the spinal rod 250 while the set screw 302 is being rotated with respect to the body 200.

In one particularly preferred embodiment, the threads formed on the externally threaded set screw 302 may incorporate inclined load flanks forming an angle with respect to the longitudinal axis 201 of the body 200. The load flanks may be converging so that the top surface of the thread and the bottom surface of the thread converge. The angle may be about five degrees (5°), although, as will be generally appreciated by one of ordinary skill in the art, the threads may take on any other form now or hereafter known for such purpose including, negative load threads, perpendicular threads flanks, buttress threads, etc.

Referring to FIGS. 1-7B, the polyaxial bone fixation element 10 is preferably provided to the user in a kit including at least (1) bone anchors, (2) locking caps, and (3) pre-assembled collet/body subassemblies. The pre-assembled collet/body subassemblies are preferably assembled by inserting the collet 150 into the axial bore 206 formed in the body 200 through the upper opening 203 formed in the body 200. The flexible arms 172 may flex inwardly as the collet 150 is inserted into the axial bore 206, if the greatest diameter of the flexible arms 172 is larger than the first diameter D1. Such a configuration generally results in the collet 150 being retained within the axial bore 206, even before the collet retention feature 50 is engaged. Once the collet 150 is positioned within the axial bore 206 such that the flexible arms 172 are positioned proximate the enlarged portion 220, a force is applied to a distal end of the partial passageway 216 formed in the body 200 so that a projection or dimple 216a is formed, which extends into the bore 206 of the body 200. The projection or dimple 216a is positioned within the longitudinal groove 175 formed in the collet 150 so that the collet 150 is free to vertically translate or float within the bore 206 with respect to the body 200, but generally prevented from passing back up through the upper opening 203 formed in the body 200 and limited in its ability to rotate relative to the body 200.

The kit is preferably shipped to the user for use in spinal surgery. During surgery, the surgeon preferably identifies a level of the spine where the surgery will take place, makes and incision to expose the selected area and implants the bone anchors 20 into the desired vertebrae 700. The body/collet subassemblies are preferably popped-on to the bone anchors 20 by urging the head 24 through the lower opening 205. Accordingly, the collet/body subassembly may be engaged with the head portion 24 of the bone anchor 20 in situ. Specifically, as the head 24 moves into the lower opening 205, the collet 150 is urged toward and into the loading position wherein the lower end of the longitudinal grooves 175 contact the dimples 216a. In the loading position, the outer curvate or spherical convex surface 151 of the collet 150 is in general vertical alignment with the enlarged curvate or spherical concave surface of the enlarged portion 220 formed in the axial bore 206 of the body 200. Alignment of the enlarged portion 220 with the collet 150 enables the collet 150 to radially or outwardly expand so that the head portion 24 of the bone anchor 20 can be received within the cavity 165 formed in the collet 150.

Once the head 24 is positioned in the cavity 165, the head portion 24 of the bone anchor 20 and the collet 150 are both preferably constrained within the body 200. The bone anchor 20 is preferably able to polyaxially rotate with respect to the collet 150 and the body 200 in this configuration. The spinal rod 250 is inserted into the rod-receiving channel 208 formed in the body 200 and onto the inner surface 161 of the seat 160. The spinal rod 250 is preferably positioned in facing engagement with the inner surface 161 of the seat 160. The set screw 302 is preferably threaded into engagement with the threads 212 formed in the body 200 to urge the spinal rod 250 and collet 150 toward the lower end 204.

Rotation of the set screw 302 causes the bottom surface of the set screw 300, preferably the saddle 310, to contact the top surface of the spinal rod 250, which in turn causes the spinal rod 250 and the collet 150 to move downwards with respect to the body 200. Downward movement of the collet 150 with respect to the body 200 causes line contact between the outer curvate or spherical convex surface 151 of the collet 150 and the first spherical undercut 218a of the lower end portion 218. Additional tightening of the set screw 300 and downward movement of the spinal rod 250 and collet 150 results in an inwardly directed compressive force to the flexible arms 172, causing the flexible arms 172 to pivot inwardly toward the head portion 24 at their terminal ends 174 about the root ends 173. In a locking position, the flexible arms 172 engage the head 24 of the bone anchor 20 securing the position of the bone anchor 20 with respect to the collet 150 and the body 200. Specifically, the flexible arms 172 of the collet 150 radially compress against the head portion 24 of the bone anchor 20, which secures the position of the bone anchor 20 with respect to the body 200. The line contact between the collet 150 and body 200 proximate the terminal ends 174 direct the radial inward force on the flexible arms 172 at a location preferably below the largest diameter of the head 24 to efficiently urge the terminal ends 174 beneath the curved outer surface of the head 24 in the locked position. In addition, the spinal rod 250 is sandwiched between the set screw 302 and the collet 150 in the locking position, thereby securing the position of the spinal rod 250 with respect to the body 200 and the bone anchor 20.

Referring to FIGS. 3 and 5A-6E, the collet 150 and body 200 may be popped-off of the bone anchor 20, in situ, after the bone fixation element 10 is engaged in the locked configuration. Specifically, the set screw 300 may be removed from the body 200 and the spinal rod 250 may be extracted from the rod-receiving channel 208 and the seat 160. A tool (not shown) engages the ledges 184, 186 and the body 200 and applies a force between the collet 150 and the body 200 to move the body 200 downwardly toward the body anchor 20. The line contact between the body 200 and the collet 150 is released and the collet 150 is urged into the loading position. In the loading position, the flexible arms 172 flex outwardly within the enlarged portion 220 to permit popping-off of the body 200 and collet 150 from the head 24 of the bone anchor 20. The collet 150 and body 200 may then be popped back onto the bone anchor 20.

Referring to FIGS. 4A, 4B and 8A-9B, the head portion 24 of the bone anchor 20 preferably includes a drive surface 30 in the form of an internal drive recess or a first tool interface 32 and a second tool interface 40. The second tool interface 40 preferably includes a plurality of threads 42 for threadably engaging the sleeve 600. The sleeve 600 preferably accommodates a variety of surgical instruments now or hereafter known including, but not limited to, the screw driver 500, a fluid delivery device such as the injection assembly 650, a compressor, a distractor, minimally invasive instrumentation, etc. By incorporating the second tool interface 40 into the head portion 24 of the bone anchor 20, the surgical instruments are able to directly engage the bone anchor 20, thus eliminating the need for the surgical instruments and/or the sleeve 600 to engage the body 200 or collet 150 of the polyaxial bone fixation element 10. In addition, once the sleeve 600 is engaged with the second tool interface 40, toggling between the screw driver 500 or another instrument inserted through an internal bore in the sleeve 600 and the bone anchor 20 is limited. In the preferred embodiment, the sleeve 600 is utilized to draw the screw driver 500 into the first tool interface 32 to limit toggling between the screw driver 500 and the bone anchor 20. The second tool interface 40 is described herein as interacting or engaging the sleeve 600, but is not so limited and may be configured to interact or engage with nearly any tool or instrument that preferably is utilized to positively engage the head 24 and apply forces to the bone anchor 20 for manipulating the bone anchor 20, vertebra 700 mounted to the bone anchor 20 or any other structure that is mounted to the bone anchor 20.

In order to facilitate implantation of the polyaxial bone fixation elements 10 and to perform, for example, one or more steps in a surgical procedure, it is advantageous to limit or remove "toggling" between the polyaxial bone fixation elements 10 and any surgical instruments that are utilized with the bone fixation elements 10. By incorporating the second tool interface 40 into the head portion 24 of the bone anchor 20, the sleeve 600 and, indirectly, the surgical instrument, for example, the screw driver 500, are directly connected to the bone anchor 20. The sleeve 600 includes a threaded distal portion 602 for threadably engaging the threads 42 of the second tool interface 40. In this manner, the sleeve 600 is directly coupled and secured to the bone anchor 20. Through this engagement, toggling is limited between the sleeve 600 and the bone anchor 20. In addition, having a close tolerance between in internal surface of the bore in the sleeve 600 and the screw driver 500 or other instrument significantly limits toggling between the screw driver 500 or other instrument and the bone anchor 20.

During the surgical procedure, the direct connection of the sleeve 600 with the bone anchor 20 facilitates protection of the polyaxial locking mechanism (the collet 150 and the body 200) of the polyaxial bone fixation element 10 and provides a more stable distraction, because the forces applied to the sleeve 600 are transferred directly to the bone anchor 20 via the second tool interface 40 and into the vertebra 700, as opposed to acting through these elements as well as the collet 150 and/or the body 200, which may distort some of the forces and cause toggling. In addition, instruments, such as the screw driver 500 or the injection assembly 650 may be securely positioned in engagement with the bone anchor 20 to drive the bone anchor 20 with the screw driver 500, inject bone cement or other fluid into and through the bone anchor 20 or otherwise conduct a procedure with the bone anchor 2, without operating through the body 200 and/or collet 150.

The second tool interface 40 preferably does not obstruct access to the drive recess 32, because the second tool interface 40 is preferably located above and radially outwardly relative to the drive recess 32. However, the second tool interface 40 is not limited to being located above and radially outwardly relative to the drive recess or first tool interface 32 and may be located below and radially inwardly relative to the first tool interface 32, as long as tools or instruments are able to engage the first and second tool interfaces 32, 40 simultaneously. Specifically, the second tool interface 40 may be comprised of a threaded recess in the bone anchor 20 having a smaller diameter and located below the first tool interface 32. Moreover, as best shown in FIGS. 9A and 9B, the sleeve 600 preferably includes the longitudinal bore so that the screw driver 500, for example, may engage the drive recess 32 formed in the head portion 24 of the bone anchor 20. In this manner, the sleeve 600 engages the bone anchor 20 via the second tool interface 40 while the screw driver 500 simultaneously engages the drive recess 32.

Referring to FIGS. 8A and 8B, the sleeve 600 is preferably associated with a slip sleeve 800 that surrounds the sleeve 600 in a working configuration. The sleeve 600 and the screw driver 500 are rotatable relative to the slip sleeve 800 such that a surgeon may grasp the slip sleeve 800 while turning a handle 502 on a distal end of the screw driver 500 to screw the bone anchor 20 into or out of the vertebra 700. When the surgeon rotates the handle 502, the sleeve 600, screw driver 500 and bone anchor 20 each rotate relative to the slip sleeve 800.

In an anchor driving position (FIG. 8B), external threads 602 on the sleeve 600 are fully threaded into the threads 42 of the second tool interface 40, thereby limiting any toggling between the sleeve 600 and bone anchor 20. The top 501 of the screw driver 500 is also fully engaged with the drive recess 32 of the bone anchor 20 in the anchor driving position. When a surgeon has completed manipulating the bone anchor 20 with the screw driver 500, the screw driver 500 may be removed from the sleeve 600 and another instrument may be utilized with the sleeve 600 to gain access to the bone anchor 20.

Referring to FIGS. 9A and 9B, the injection assembly 650 may be utilized with the sleeve 600 to inject bone cement or other flowable materials into a cannulated bone anchor 20'. Once the bone anchor 20' is mounted in the vertebra 700 and the sleeve 600 is mounted on the bone anchor 20', a cannula 652 of the injection assembly 650 is inserted into the sleeve 600. The cannula 652 is associated with a syringe 654 at a proximal end and includes a blunt tip 656 at a distal end. The cannula 652 preferably includes an engagement mechanism 656 proximate the proximal end to engage a proximal end of the sleeve 600 to secure the cannula 652 to the sleeve 600. In addition, the engagement mechanism 656 preferably urges the blunt tip 656 of the cannula 652 into engagement with a shelf 32a at the bottom of the first tool interface 32 such that a flow channel 34 of the cannula 652 is in communication with a flow channel 652a of the cannula and a seal is created between the blunt tip 656 and the shelf 32a. In the preferred embodiment, the engagement mechanism 656 is comprised of a threaded joint that may be tightened to secure the cannula 652 relative to the sleeve 600 and securely seal the blunt tip 656 to the shelf 32a, thereby generally preventing leakage of bone cement or other flowable fluid into the first tool interface 32. Bone cement is preferably injected into the flow channel 652a with the injection assembly 650 and into the vertebra 700 to securely mount the bone anchor 20' to the vertebra 700, particularly in generally weak, brittle and/or osteoporotic bone. The bone anchor 20' may also be fenestrated to inject bone cement toward the sides of the bone anchor 20' or to generally directionally dispense the bone cement or other fluid. Further, the bone anchor 20' may be utilized to extract material from the vertebra 700 or other bone that the bone anchor 20' is engaged with by drawing the material into the flow channel 652a, by, for example, creating a vacuum in the flow channel 652a. For example, the bone anchor 20' may be utilized to extract bone marrow from the bone. Further, the bone anchor 20' may be utilized to aid in bone graft extension, as would be apparent to one having ordinary skill in the art.

It should be understood that while the bone anchor 20 is being described herein as preferably including the second tool interface 40, the second tool interface 40 is optional. Furthermore, it should be understood that the bone anchor 20 including the second tool interface 40 may be used in any other type of bone screw application such as, for example, long bone fixation, fracture fixation, or in connection with securing a bone plate, vertebral spacer, dental implant, etc.

The polyaxial bone fixation element 10 including the bone anchor 20, the collet 150, the body 200 and the locking cap 300 may be made from any biocompatible material now or hereafter known including, but not limited to, metals such as, for example, titanium, titanium alloys, stainless steel, Nitinol, etc.

As will be appreciated by those skilled in the art, any or all of the components described herein may be provided in sets or kits so that the surgeon may select various combinations of components to perform a fixation procedure and create a fixation system which is configured specifically for the particular needs/anatomy of a patient. It should be noted that one or more of each component may be provided in a kit or set. In some kits or sets, the same device may be provided in different shapes and/or sizes.

While the foregoing description and drawings represent the preferred embodiment of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the appended claims.

The invention claimed is:

1. An assembly configured to be connected to an elongated spinal rod, the assembly comprising:
   a body that is elongate along a longitudinal axis, the body including an upper end with an upper opening, a lower end with a lower opening, the body defining a bore that is elongate along the longitudinal axis and disposed between the upper and lower openings, the bore defining a first diameter proximate the upper opening and the bore further defining a rod-receiving channel extending from the upper end toward the lower end, the rod-receiving channel disposed along a channel axis that is oriented substantially perpendicular to the longitudinal axis, the bore at least partially defined by a lower edge portion of the body, the lower edge portion of the body defining a first curved inner surface that forms a first spherical undercut disposed proximate the lower end, the bore further at least partially defined by an enlarged diameter portion of the body, the enlarged diameter portion of the bore defining a second curved inner surface that forms a second spherical undercut, wherein the second spherical undercut is spaced toward the upper end from the first spherical undercut, the bore has a second diameter at the first curved inner surface of the lower edge portion, and the bore has a third diameter at the second curved inner surface of the enlarged diameter portion, the third diameter is larger than the first diameter, and the first diameter is larger than the second diameter; and a collet defining a cavity that is sized to receive a head portion of a bone anchor and including an expandable portion that is expandable to accept the head portion of the bone anchor and compressible to secure the head portion of the bone anchor relative to the collet, wherein the collet is configured to move within the bore between a loading position, where the expandable portion is proximate the enlarged diameter portion, thereby allowing the head portion to move within the cavity, and a locked position, where part of the expandable portion is in line contact with at least a portion of the first curved surface and the expandable portion is compressed against the head portion such that the head portion is unable to move within the cavity.

2. The assembly of claim 1, further comprising a collet retention feature that extends into the bore between the upper end and the second undercut that prevents the collet from passing through the upper opening in an assembled configuration.

3. The assembly of claim 2, wherein the collet retention feature contacts a bottom end of a groove in the collet in the loading position to align the expandable portion with the second spherical undercut.

4. The assembly of claim 1, wherein the collet defines a first end, a second end spaced opposed to the first end along the longitudinal axis, and a collet bore that extends from the first collet end to the second collet end along the longitudinal axis, the collet bore at least partially defining the cavity.

5. The assembly of claim 4, wherein the collet defines a first collet end, a second collet end spaced opposed to the first end along the longitudinal axis, wherein the body includes the one or more projections, the one or more projections configured to engage the collet at a location between the first collet and the second collet end to inhibit the collet from moving back through the upper opening formed in the body.

6. The assembly of claim 1, further comprising:
a locking cap removably engageable with the body, the locking cap being movable from an unlocked position to a locked position wherein movement of the locking cap from the unlocked position to the locked position moves the collet from the loading position to the locked position.

7. The assembly of claim 1, wherein the expandable portion includes a plurality of flexible arms that are configured to move toward and away from one another.

8. The assembly of claim 7, wherein the collet includes a collet body, the collet body defines a first end, a second end opposite the first end, and at least two slots that extends through the collet body to define the flexible arms, the at least two slots being elongate along a direction from the second end toward the first end.

9. The assembly of claim 7, wherein at least one of the flexible arms defines an outer convex surface that is configured to be in line contact with a portion of the first curved surface when the collet is in the locked position.

10. The assembly of claim 9, wherein the outer convex surface has a substantially spherical shape.

11. The assembly of claim 1, wherein the second spherical undercut is disposed adjacent the first spherical undercut, such that the lower end of the lower edge portion defines a boundary therebetween.

12. The assembly of claim 1, wherein the first curved inner surface is curved with respect to the longitudinal axis and has a first radius of curvature, wherein the second curved inner surface is curved with respect to the longitudinal axis and has a second radius of curvature that is greater than the first radius of curvature.

13. The assembly of claim 1, further comprising the bone anchor, wherein the head portion of the bone anchor is an enlarged, curvate head portion including a first tool interface configured to engage a first surgical instrument so as to couple the bone anchor to the first surgical instrument and a second tool interface configured to engage a second surgical instrument so as to couple the bone anchor to the second surgical instrument, the first and second tool interfaces positioned in a head interface cavity.

14. The assembly of claim 13, wherein the first tool interface includes a drive surface which is an internal surface formed in the head portion of the bone anchor, the drive surface configured to receive an external tip formed on the first surgical instrument, and the second tool interface is a plurality of threads formed on the head portion, the plurality of threads configured to threadedly engage a portion of the second surgical instrument.

15. The assembly of claim 13, wherein the second tool interface is located proximal of the first tool interface so that the second tool interface does not obstruct access to the first tool interface.

16. The assembly of claim 13, further comprising the second surgical instrument, wherein the second surgical instrument is selected from one of a compressor, a distractor, a screw driver, a sleeve, minimally invasive instrumentation, a bone augmentation tool, an aspiration tool, a reduction tool, a coronal rotation tool, a tissue retractor and a kyphosis or lordosis correction tool.

17. The assembly of claim 1, wherein the first spherical undercut has a first radius of curvature and wherein the expandable portion of the collet defines an outer curvate convex surface having a second radius of curvature, wherein the first radius of curvature is different than the second radius of curvature.

18. The assembly of claim 1, wherein the collet includes an outer surface and a pair of longitudinal grooves on the outer surface, the body includes a pair of dimples that extend into the bore, each of the dimples is configured to be disposed in one of the longitudinal grooves so as to couple the body to the collet.

19. An assembly configured to be connected to an elongated spinal rod, the assembly comprising:
a body that is elongate along a longitudinal axis, the body including an upper end with an upper opening, a lower end with a lower opening, the body defining an inner surface that is spaced from the longitudinal axis of the body such that the inner surface at least partially defines a bore that is elongate along the longitudinal axis and disposed between the upper and lower openings, the bore defining a first diameter proximate the upper opening and the bore further defining a rod-receiving channel extending from the upper end toward the lower end, the rod-receiving channel disposed along a channel axis that is oriented substantially perpendicular to the longitudinal axis, the bore at least partially defined by a lower edge portion of the body, the bore further at least partially defined by an enlarged diameter portion of the body that is spaced toward the upper end from the lower end of the body, the inner surface having a first spherical undercut disposed at the lower edge portion of the body, the first spherical undercut being curved with respect to the longitudinal axis so as to define a first radius of curvature, the inner surface further having a second spherical undercut disposed in the enlarged diameter portion of the body, the second spherical undercut being spaced from the first spherical undercut toward the upper end of the body, the second spherical undercut being curved with respect to the longitudinal axis so as to define a second radius of curvature that is greater than the first radius of curvature, wherein the bore has a second diameter at the lower edge portion and a third diameter at the enlarged diameter portion, wherein the third diameter is larger than the first diameter, and the first diameter is larger than the second diameter; and a collet defining an upper end, a lower end spaced from the upper end along a collet longitudinal axis, a collet bore extending from the upper end to the lower end along the collet longitudinal axis, the collet bore at least partially defining a cavity that is sized to receive a head portion of a bone anchor, the collet including an expandable portion proximate the lower collet end, the expandable portion is expandable to accept the head portion of the bone anchor and compressible to secure the head portion of the bone anchor relative to the collet, wherein the collet is configured to move within the bore between a loading position, where the expandable portion is proximate the enlarged diameter portion, thereby allowing the head portion to move within the cavity, and a locked position, where part of the expandable portion is in line contact with at least a portion of the lower edge portion of the body and the expandable portion is compressed against the head portion such that the head portion is unable to move within the cavity.

20. The assembly of claim 19, further comprising a locking cap removably engageable with the body, the locking cap being movable from an unlocked position to a locked position wherein movement of the locking cap from the unlocked position to the locked position moves the collet from the loading position to the locked position.

21. The assembly of claim 20, wherein the locking cap is removably engageable to the upper end of body.

22. The assembly of claim 19, wherein the collet includes a collet body that extends between the upper end the lower end, the collet body defining at least two slots that extends through the collet body to define at least one flexible arm, the at least two slots being elongate along a direction from the lower end to the upper end.

23. The assembly of claim 22, wherein at least one of the flexible arms defines a terminal end, wherein the terminal end of the flexible arm is configured to contact a portion of the lower end of the body when the collet is in the locked position.

24. The assembly of claim 22, wherein the collet body defines an outer convex surface that has a substantially spherical shape.

25. The assembly of claim 19, wherein collet defines a rod seat disposed at the upper collet end for receiving a rod.

26. The assembly of claim 19, wherein the second spherical undercut is disposed adjacent the first spherical undercut to define a circumferential boundary therebetween.

27. The assembly of claim 19, further comprising the bone anchor, wherein the head portion of the bone anchor is an enlarged, curvate head portion including a first tool interface configured to engage a first surgical instrument so as to couple the bone anchor to the first surgical instrument and a second tool interface configured to engage a second surgical instrument so as to couple the bone anchor to the second surgical instrument, the first and second tool interfaces positioned in a head interface cavity.

28. The assembly of claim 27, wherein the first and second surgical instruments are configured for insertion through the bore of the body and the bore of the collet to engage with the head portion of the bone anchor.

\* \* \* \* \*